(12) United States Patent
Schwarz et al.

(10) Patent No.: US 7,504,095 B2
(45) Date of Patent: Mar. 17, 2009

(54) METHOD FOR OBTAINING PRECURSOR Z AND USE THEREOF FOR THE PRODUCTION OF A MEANS FOR THERAPY OF HUMAN MOLYBDENUM COFACTOR DEFICIENCY

(75) Inventors: Guenter Schwarz, Niederkassel (DE); Ralf Mendel, Leitferde (DE); José Santamaria, Köln (DE); Jochen Reiss, Niemetal (DE)

(73) Assignee: Technische Universitaet Braunschweig, Braunschweig (DE)

( * ) Notice: Subject to any disclaimer, the term of this patent is extended or adjusted under 35 U.S.C. 154(b) by 0 days.

(21) Appl. No.: 11/343,489

(22) Filed: Jan. 31, 2006

(65) Prior Publication Data

US 2007/0037250 A1   Feb. 15, 2007

Related U.S. Application Data

(63) Continuation of application No. PCT/DE2005/000142, filed on Jan. 31, 2005.

(30) Foreign Application Priority Data

Jan. 29, 2004 (DE) .............. 10 2004 004 642
Jan. 30, 2004 (DE) .............. 10 2004 063 948

(51) Int. Cl.
*A61K 31/74* (2006.01)
*A61K 31/785* (2006.01)
*A61K 31/77* (2006.01)

(52) U.S. Cl. .............. 424/78.08; 424/78.36; 424/78.38

(58) Field of Classification Search .................. None
See application file for complete search history.

(56) References Cited

OTHER PUBLICATIONS

Pitterle et al., In vitro synthesis of molybdopterin from precursor Z using purified converting factor, Journal of Biological Chemistry, 1993, 268(18): 13506-13509.*
Spector et al., Journal of Biological Chemistry, vol. 250, No. 8, Issue of Apr. 26, pp. 3101-3107, 1975.*
"GMP" chemical structure, Retrieved from the Internet <http://www.ebi.ac.uk/chebi/searchld.do?chebild=CHEBI:17345>, [Retrieved on Mar. 31, 2008].*
Leimkuhler et al., J. Biol. Chem., 276(25), pp. 22024-22031, 2001.*
Wuebbens et al., Structural Characterization of a Molybdopterin Precursor, J. Biol. Chem., vol. 268, No. 18, Jun. 25, 1993, pp. 13493, 13498.
Hänzelmann et al., Functionality of Alternative Splice Forms of the First Enzymes Involved in Human Molybdenum Cofactor Biosynthesis, J. Biol. Chem., vol. 277, No. 21, May 24, 2002, pp. 18303-18312.
Schwarz et al., Rescue of Lethal Molybdenum Cofactor Deficiency by a Biosynthetic Precursor from *Escherichia coli*, Human Molecular Genetics, vol. 13, No. 12, 2004, pp. 1249-1255.
Santamaria-Araujo et al., The Tetrahydropyranopterin Structure of the Sulfur-free and Metal-free Molybdenum Cofactor Precursor, J. Biol. Chem., vol. 279, No. 16, Apr. 16, 2004, pp. 15994-15999.
Wuebbens et al., Mechanistic and Mutational Studies of *Escherichia coli* Molybdopterin Synthase Clarify the Final Step of Molybdopterin Biosynthesis, J. Biol. Chem., vol. 278, No. 16, Apr. 18, 2003, pp. 14523-14532.
Gutzke et al., Der Zweite schritt der Molybdancofaktor-Biosynthese: Molekularer Mechanismus der Konversion von Precursor Z zu Molybdopterin, Dissertation, Carolo-Wilhelmina University, Braunschweig, Germany, Apr. 2, 2002 (Abstract).

* cited by examiner

*Primary Examiner*—Delia M Ramirez
*Assistant Examiner*—Jae W Lee
(74) *Attorney, Agent, or Firm*—Patent Central LLC; Stephan A. Pendorf

(57) ABSTRACT

The invention relates to a method for obtaining the molybdopterin derivative precursor Z, wherein an over-production of precursor Z occurs in host organisms by recombinant expression of precursor Z synthesizing proteins. The invention further relates to the use of precursor Z for the production of a means for the therapy of human molybdenum cofactor deficiency and associated diseases, which may be directly or indirectly attributed to an altered molybdenum cofactor synthesis, whereby precursor Z is used as essential component of said therapy means.

2 Claims, 13 Drawing Sheets

E

Precursor Z ($C_{10}H_{14}N_5O_8P$ = 363 Da)

↓ oxidation

Compound Z ($C_{10}H_{14}N_5O_7P$ = 343 Da)

Figure 1:
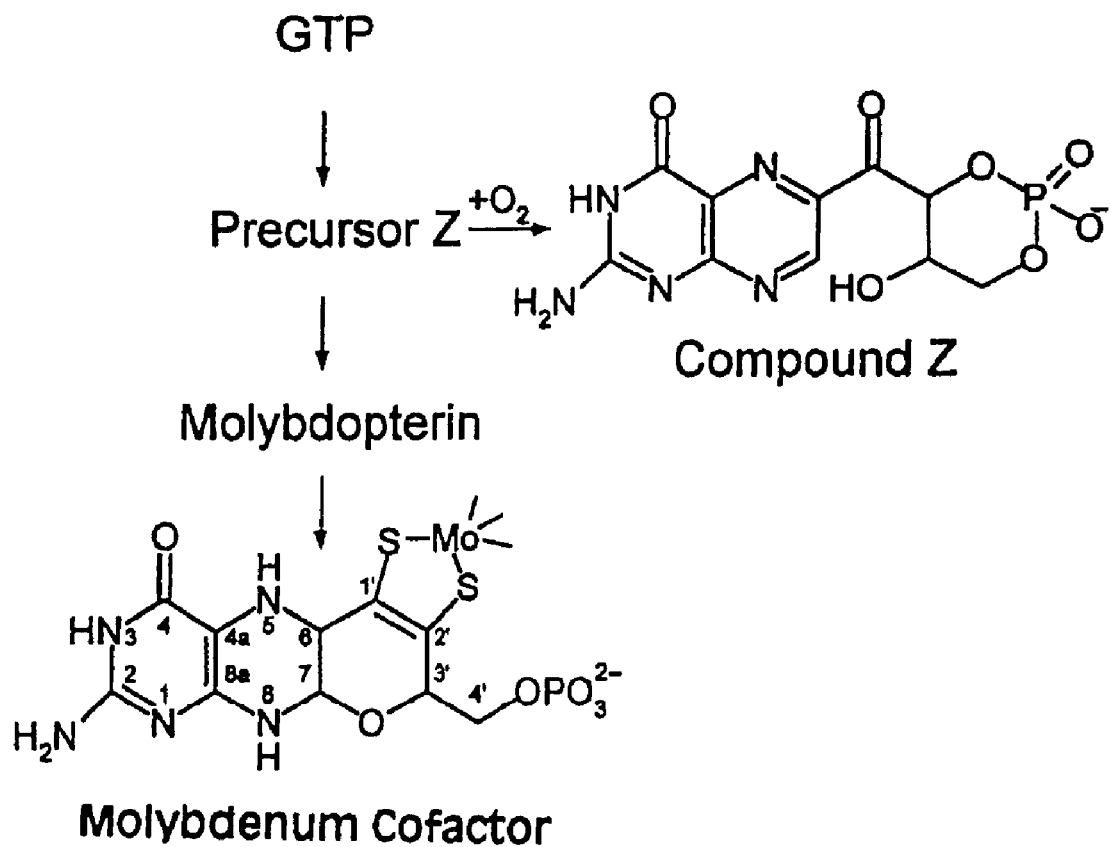

METHOD FOR OBTAINING PRECURSOR Z AND USE THEREOF FOR THE PRODUCTION OF A MEANS FOR THERAPY OF HUMAN MOLYBDENUM COFACTOR DEFICIENCY

CROSS-REFERENCE TO RELATED APPLICATIONS

This application is a continuation of International Patent Application No. PCT/DE2005/000142 filed Jan. 31, 2005 which claims priority from German Patent Application No. DE 10 2004 004 642.5 filed Jan. 29, 2004 and German Patent Application No. DE 10 2004 063 948.5 filed Jan. 30, 2005.

The invention relates to a method for obtaining the molybdopterin derivative precursor Z.

The invention further relates to the use of precursor Z for the production of a means for the therapy of human molybdenum cofactor deficiency and associated diseases, which may be directly or indirectly attributed to an altered molybdenum cofactor synthesis.

Molybdenum cofactor (Moco), an evolutionarily highly conserved molybedenum (Mo) coordinated pterin-compound, is necessary for the activity of all Mo-enzymes with the exception of nitrogenase. Moco is produced by a unique and evolutionarily ancient multi-step synthesis pathway, from which until now two intermittents have been identified: the sulphur- and metal-free pterin derivative precursor Z and molybdopterin (MPT), a pterin with a ene-dithiol function, which is essential for the Mo-linkage. The latter pterin component presumably forms a pyronopterin similar to Moco, which has been found in the crystal structures of Mo-enzymes. MPT likewise coordinates tungsten (W) in W-dependent enzymes.

It is the task of the present invention to provide a process for obtaining the molybdopterin derivative precursor Z.

This task is solved in conjunction with pre-characterizing portion of claim 1 thereby, that precursor Z is over-produced in host organisms by recombined expression of precursor Z synthesizing proteins.

Thereby it is possible to make precursor Z available in a sufficient amount for further use.

According to a preferred embodiment of the invention, as the host organism a bacterial strain, for example bacteria E. coli is employed, which accumulates precursor Z on the basis of a defect in the conversion to molybdopterin (MPT).

In the host organism there occurs simultaneously a recombinant expression of the bacterial proteins MoaA and MoaC, or their homologs, in the host organisms with a defect in a second step of the molybdenum cofactor (Moco) biosynthesis.

According to a further preferred embodiment of the invention, the culturing of the host organisms occurs under anaerobic conditions, at low temperatures and low IPTG-inductor concentrations. Preferred are temperatures of less than 20° C.

The molecular formula of precursor Z is $C_{10}H_{14}N_5O_8P$ represents a pyranopterin carrying a geminal (two identical constituents on the same carbon change) diol in the side chain.

According to a preferred embodiment of the invention, the precursor Z is chromatographically purified and subsequently concentrated. Therein the precursor Z is isolated by acidic extraction from the host organism and subsequently separated chromatographically on a HPLC reverse phase column with citrate buffer.

According to a further embodiment, precursor Z containing fractions are subject to chromatography in a further step in a HPLC anion exchange column (SAX) and subsequently concentrated in a reverse phase/anion exchange column.

Replacement therapies for illnesses, inclusive of methods for replacement of enzymes, are frequently limited by the limited availability of the therapeutic active agents.

Molybdenum cofactor (Moco) deficiency is a pleiotropic genetic disorder, which is characterized by the loss of the molybdenum dependent enzymes sulphite-oxidate, xanthine oxidoreductase and aldehyde oxidase due to the mutations in Moco biosynthesase genes. An intermediate of this biosynthesis pathway, "precursor Z," is more stable than the cofactor itself and has a conserved structure in all phyla. For this reason, the substance is produced in the bacterial E. coli, purified, and used for treatment of precursor Z-deficient "knockout" mice, which display a phenotype resembling that of the human deficiency state. Precursor Z treated mice achieve the adult stage and are capable of transplantation. Biochemical and morphological analyses as well as examination of the behaviour support the premise, that the described treatment is suitable for attenuation of most symptoms of human Moco deficiency.

All molybdenum (Mo) containing enzymes of humans, animals, plants, arachaea and bacteria, with prokaryotic nitrogenase as sole exception, require a cofactor, which is comprised of an organic moiety, the so-called molybdopterin (MPT), and molybdenum.[B1] This unique and "universal" molybdenum cofactor (Moco) possesses an all phylogenetic groups the same base structure that is very instable in its free form, in particular under aerobic conditions insofar as it is not bound to a apo-protein.[B2] The multi-step biosynthetic pathway, via which a guanosine derivative is converted into active Moco, is evolutionarily conserved[B1] and the corresponding proteins from various organisms involved in Moco synthesis are extremely homologous [B3-B7]. A mutational defect in Moco-biosynthesis leads to simultaneous loss of the activities of all Mo enzymes, inclusive the sulphite oxidaes[B8, B9]. Human Moco deficiency is a severe, autosomal-recessive genetic disorder, which clinically cannot be differentiated from the less frequently occurring sulphite-oxidaes difficiency[B10-B12]. Although a few less severe cases are known[B13], most afflicted patients exhibit neurological abnormalities such as non-treatable seizures and lack of development of the brain, which can be traced back to the toxicity of sulphite, a lack of sulphate or, as the case may be, both. Until the present day no effective therapy has been available, for which reason afflicted patients as a rule die in early childhood[B14].

The first eukaryotic gene of the Moco-biosynthesis, which could be isolated, originated from the plant Arabidopsis thaliana[B15]. A search for homologous sequences led to identification of the first human gene involved in Moco-biosynthesis, MOCS1[B3]. The gene products MOCS1A and MOCS1B, the expression of which involved a complicated pattern of alternative splices[B16-B18], converted a guanosine derivative into the sulphur-free precursor Z, which already exhibited the unique side chain of the MPT comprised of four C-atoms[B19]. Mutations in the MOCS1-gene were detected in two-thirds of the Moco-deficient patients, which represents the complementation group A or as the case may be, the Moco-deficiency type A[B10, 20]. In a subsequent step, precursor Z was converted to MPT; this occurs by an enzyme, which is encoded by MOCS2-gene, which is activated by the MOCS3-gene product[B4]. The majority of the type B-patients carry MOCS2-mutations[B12, 13, B21]. Finally, Mo is inserted into MPT by the multifunctional protein gephyrin [B5]. Until now, only one family with mutations in the gephyrin-gene (GEPHN), which leads to Moco-deficiency (Type C)[B22], has been described.

As a consequence of mutations in various steps of the Moco biosynthesis, it was discovered, that fibroblasts of type B patients accumulate precursor Z and elliptis into the culture medium; this can be taken up by type A-cells in the course of a co-cultivation, which leads to reestablishment of Mo-enzyme activities in vivo[B20]. Further, it could be demonstrated that precursor Z from human fibroblasts was identical with the bacterial precursor $Z^{B23, B24}$, since this biosynthesis occurs conserved or homologously in all organisms[B15-B17].

It is further the task of the invention to provide a means for a therapy of human molybdenum cofactor deficiency and associated afflictions, which can be traced directly or indirectly to an altered molybdenum cofactor synthesis.

This task with regard to the pre-characterizing portion of claim 12 is solved thereby, that precursor Z is employed as essential component of this means.

Therewith it is for the first time possible to provide means for therapy of human molybdenum cofactor deficiency and associated afflictions, which directly or indirectly can be traced back to an aberant molybdenum cofactor synthesis. Described is the obtaining of a pterin intermediate from bacteria, which is successfully employed for therapy of a hitherto incurable and deadly ailment.

Further uses of the invention can be seen from the following detailed description and the associated figures, in which preferred embodiments of the invention are illustrated for exemplary purposes.

The figures show:

FIG. 1: General diagram of Moco-biosynthesis. The structures of Moco (as found in the crystal structure of Mo-enzymes) and the precursor Z oxidation product compound Z (14, 15) are shown. The numbering is shown and employs the same numbering scheme as standard pterin; for discussion see (12).

FIG. 2: ESI-MS of precursor Z. A, MS-spectrum of the purified precursor Z and structural association of the essential molecular ions. B, MS/MS-spectrum of the main peaks at 364 Da, which is shown in (A) and structural association of the main fragment ions. The spectra were recorded in the positive ion mode. Thus all shown molecular fragment ions are shown as nuetral molecules, and not in $[M+H]^+$-mode as in the spectra.

Figure 3A:
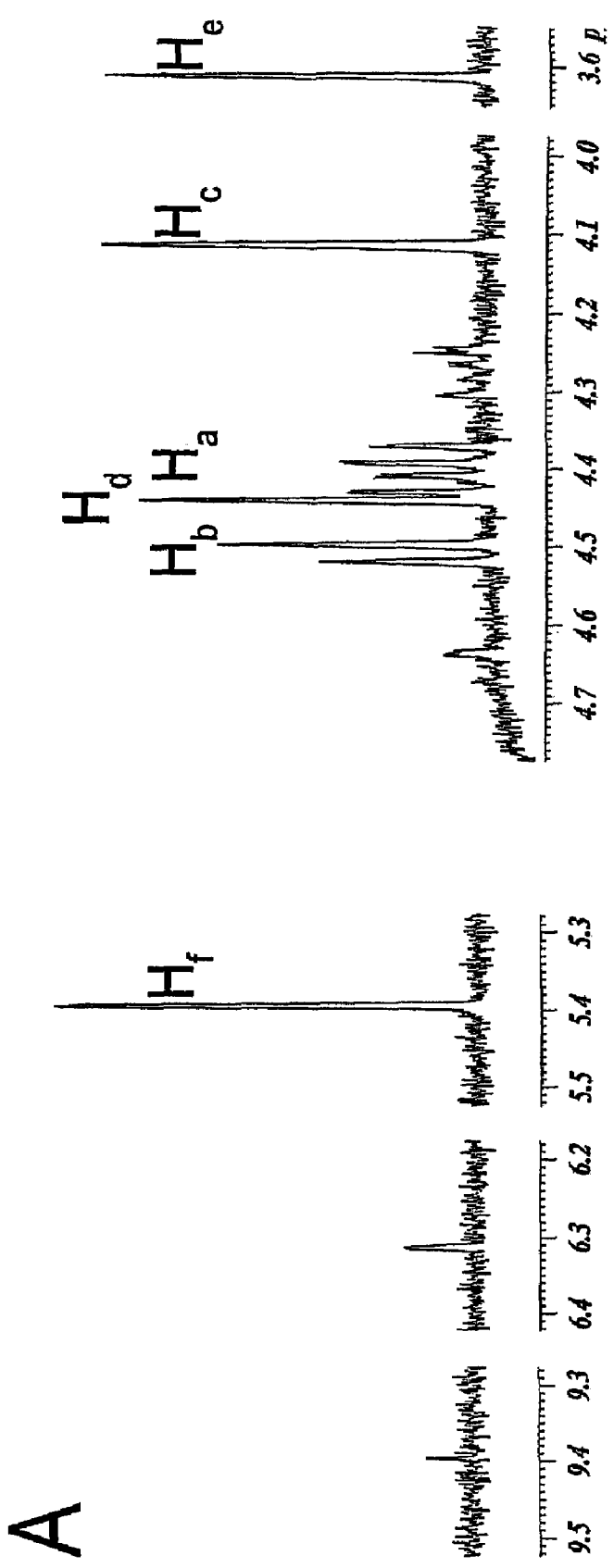
Figure 3:
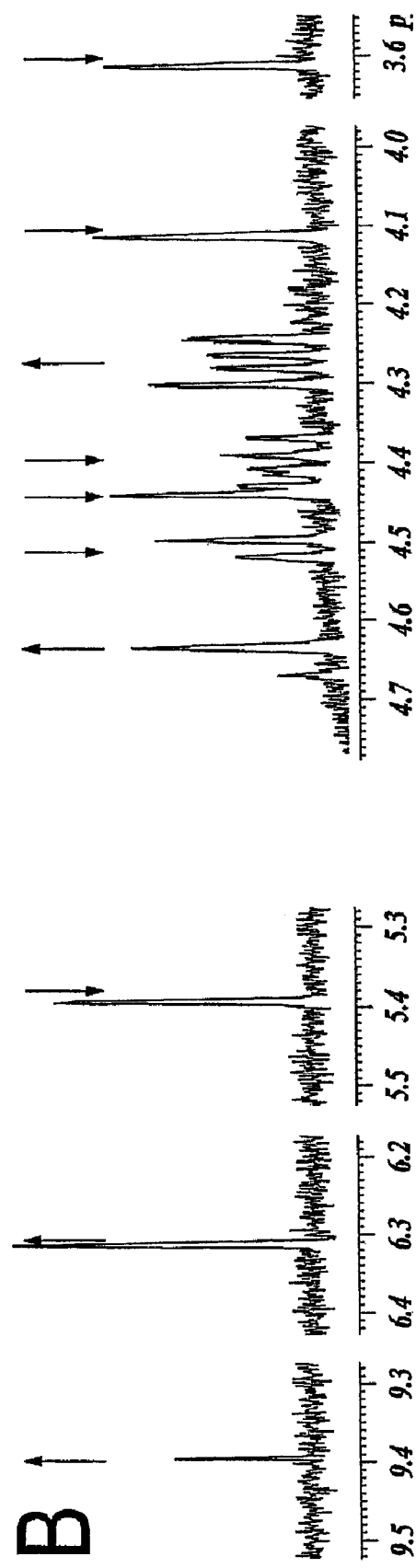
Figure 3:
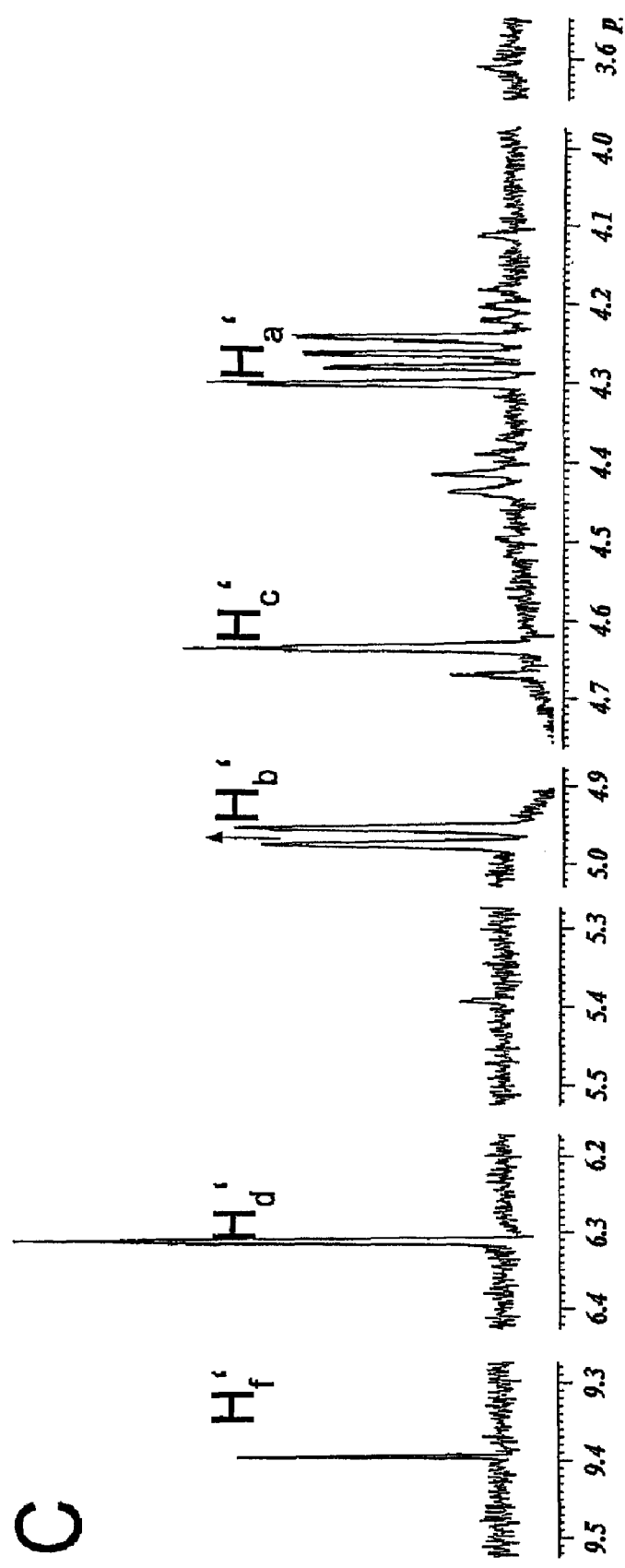
Figure 3:
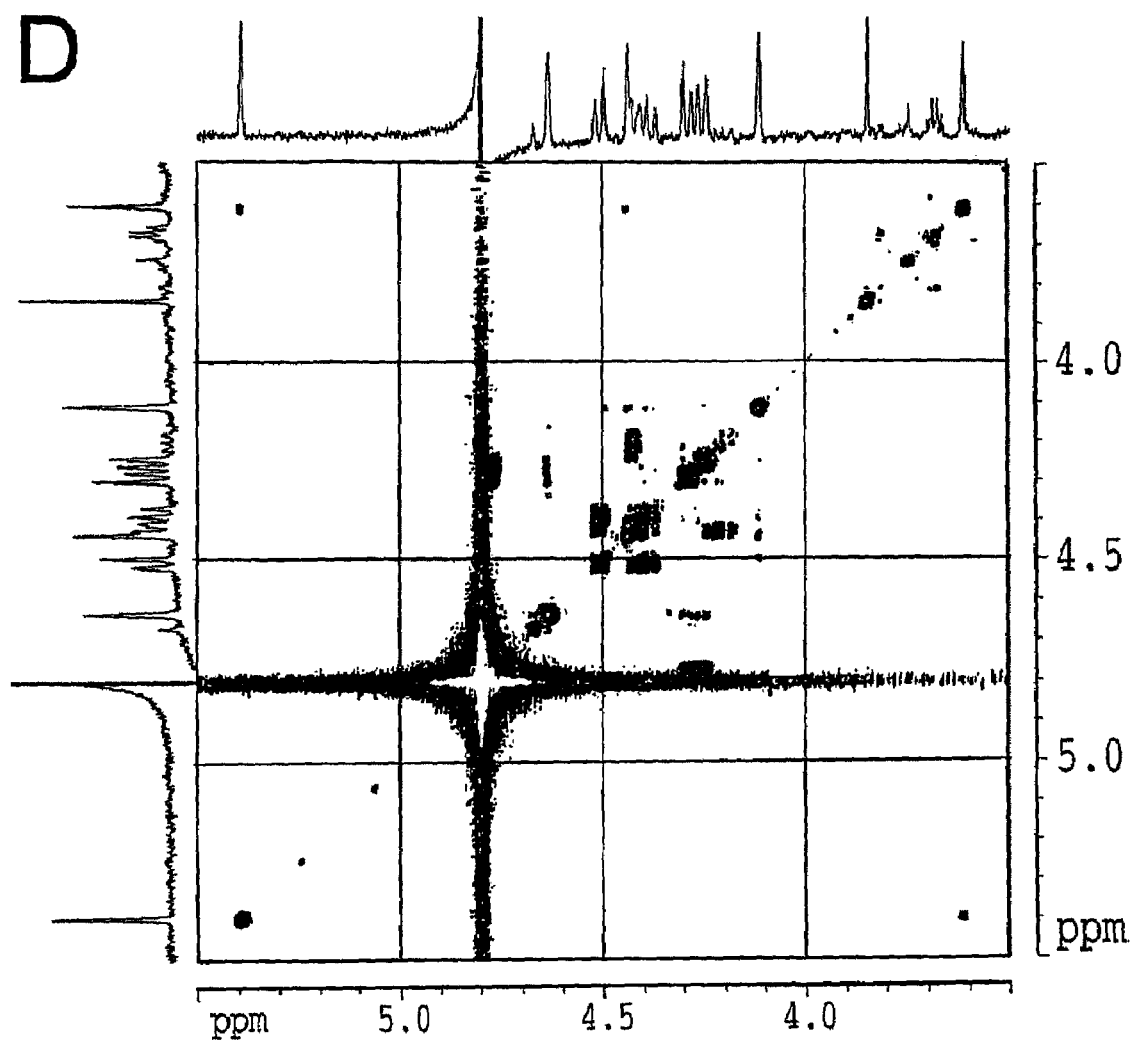
Figure 3:
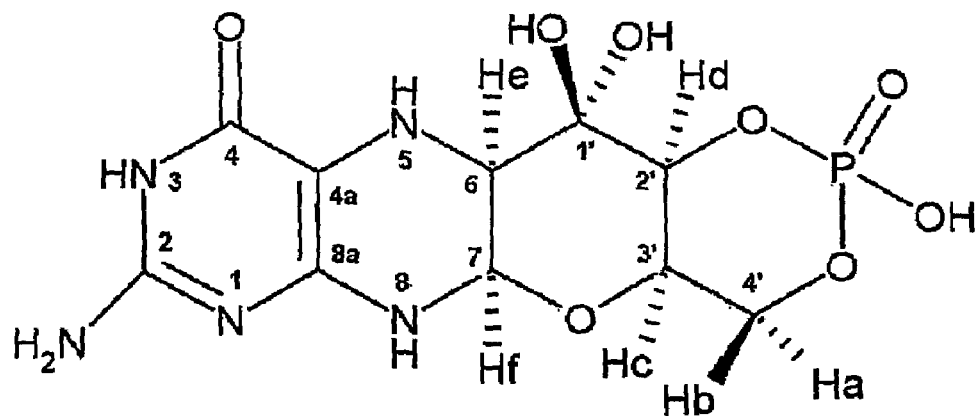
Figure 3:
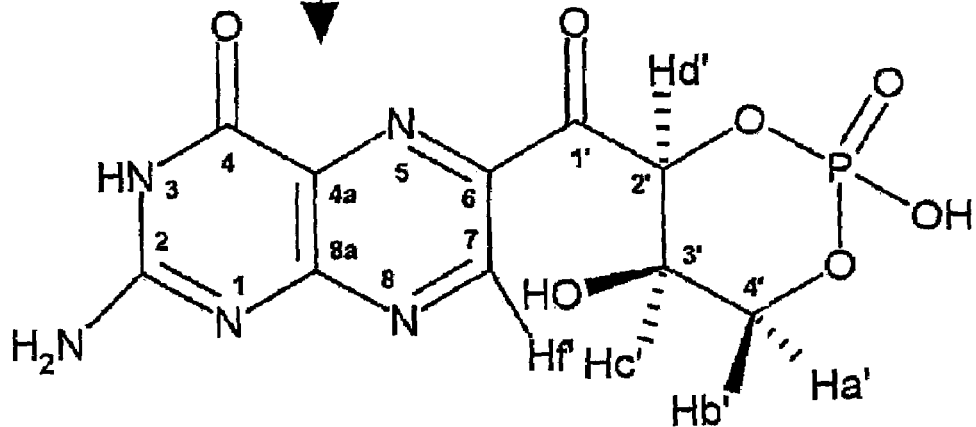

FIG. 3: $^1$H-NMR and Correlation Spectroscopy at 300 K of precursor Z (A), of partial oxidized precursor Z (B) and its stable oxidation product compound Z (C). A-C, the 1D-$^1$H-NMR spectrum of precursor Z was recorded with a 150 μg sample, dissolved in 700 μl D$_2$O and acidified to pH 1 by addition of 2 μl 36% DCl. The measurements were repeated following partial (14 hours, B) and complete oxidation (14 days, C). The relevant areas of all three spectra are shown. Note: A doublet of triplet-signals of H$_b$' in compound Z lies below the background signal of water at 300 K, however, it is clearly visible at 315 K (C 5.0-5.1 ppm in C). D, 2D-COSY-$^1$H-NMR-spectrum of the partially oxidized precursor Z sample from (B). E, structure of precursor Z as determined by ESI-MS- and $^1$H-NMR-spectroscopy as well as by the structure of the oxidation product of compound Z. The naming of the protons is the same as in A (precursor Z) and C (compound Z) as well as in Table 1 and in the text. Compound Z-protons are marked with a dash or line, in order to distinguish them from those of precursor Z.

Figure 4:
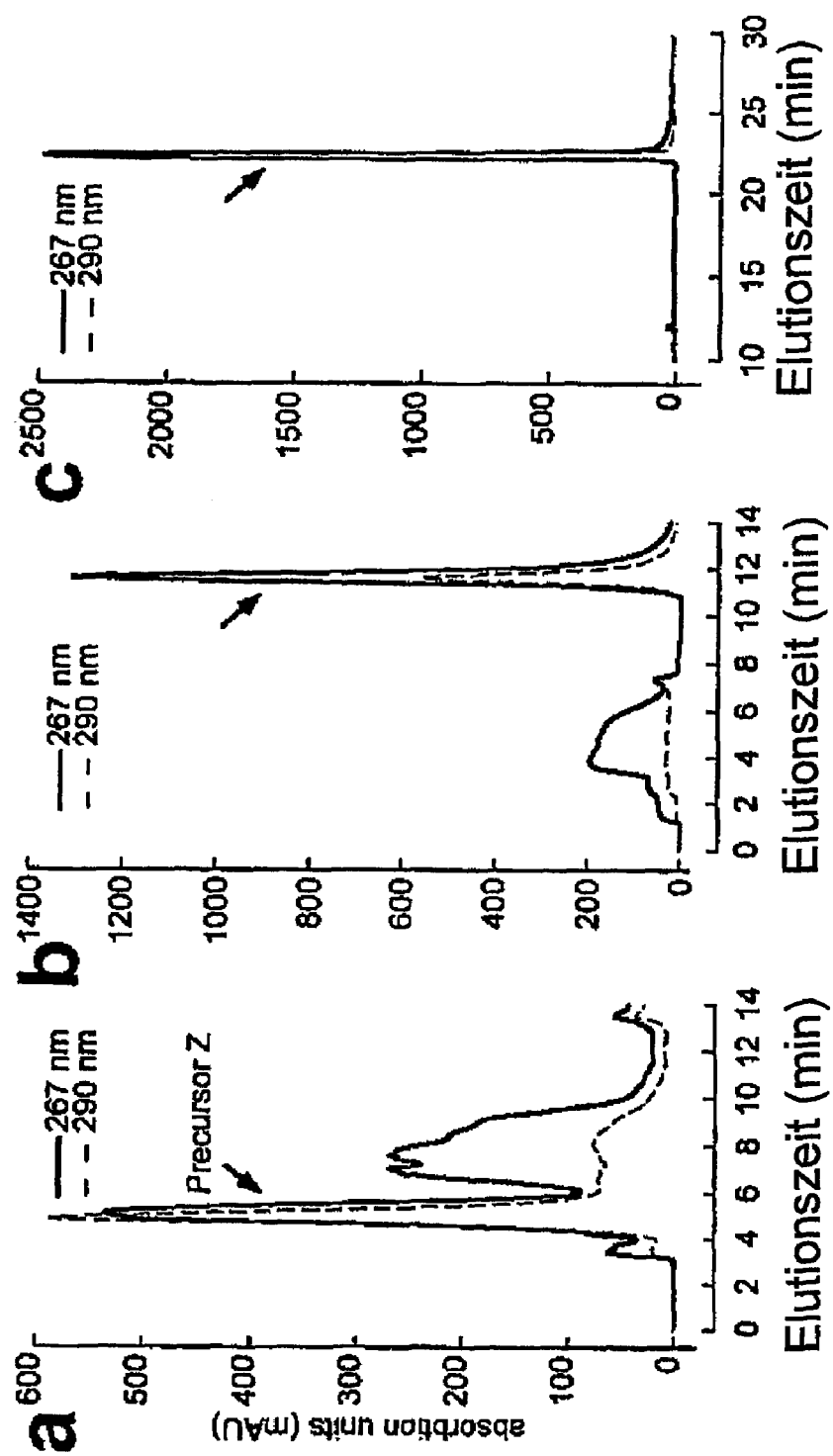

FIG. 4: HPLC-purification of precursor Z from E. coli MJ7 ch1M (DE3) 37 cells, which contain pPH15moaA and pPHLysmoaC. (a) Elution profile of a preparative C8 column. (b) Elution profile of a SAX column. (c) Elution profile of an analytic C18 column. For details see the methods.

Figure 5:
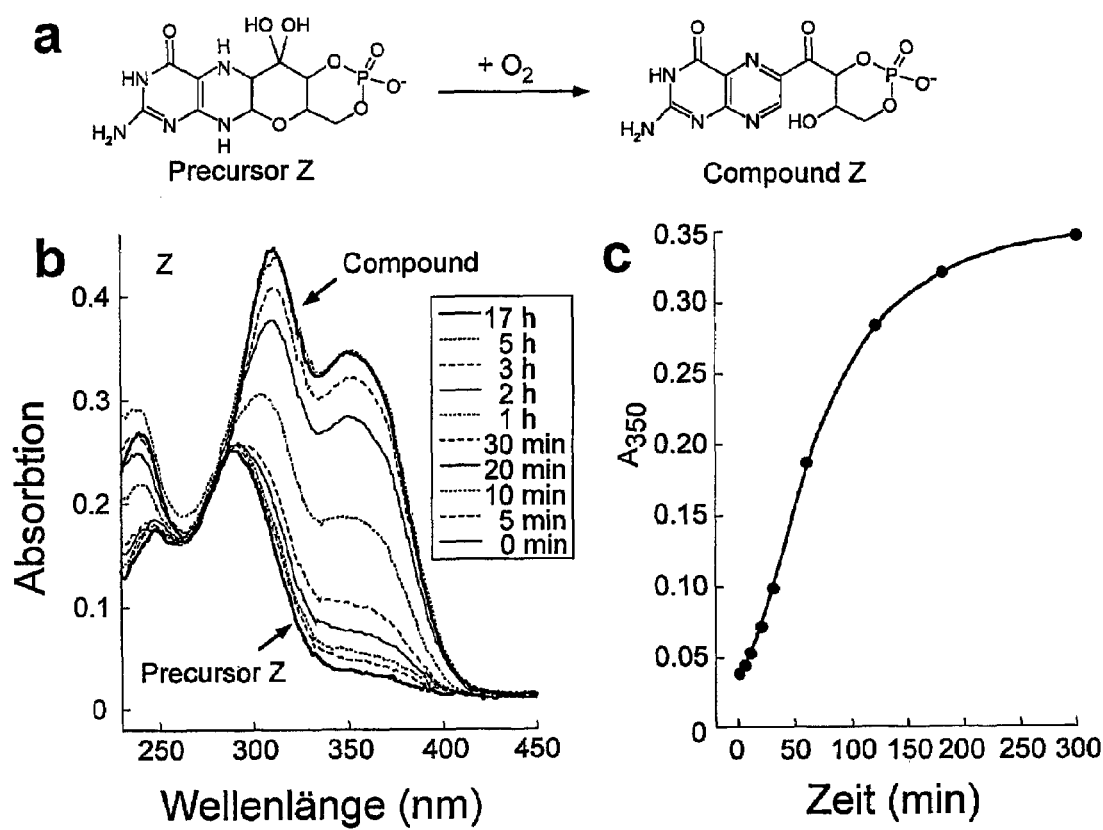

FIG. 5: Purified precursor Z is stable under physiological conditions. (a) Oxidation of precursor Z to compound Z. (b) UV-VIS absorption spectrum of 22 μM precursor Z after 17 h incubation at room temperature in 2× PBS-Buffer (pH 6.9). The spectra were recorded and indicated in time intervals following dilution in Buffer. (c) Clinical analysis of oxidation of precursor Z by recording the absorption at 350 nm from the spectra shown in (b).

Figure 6:
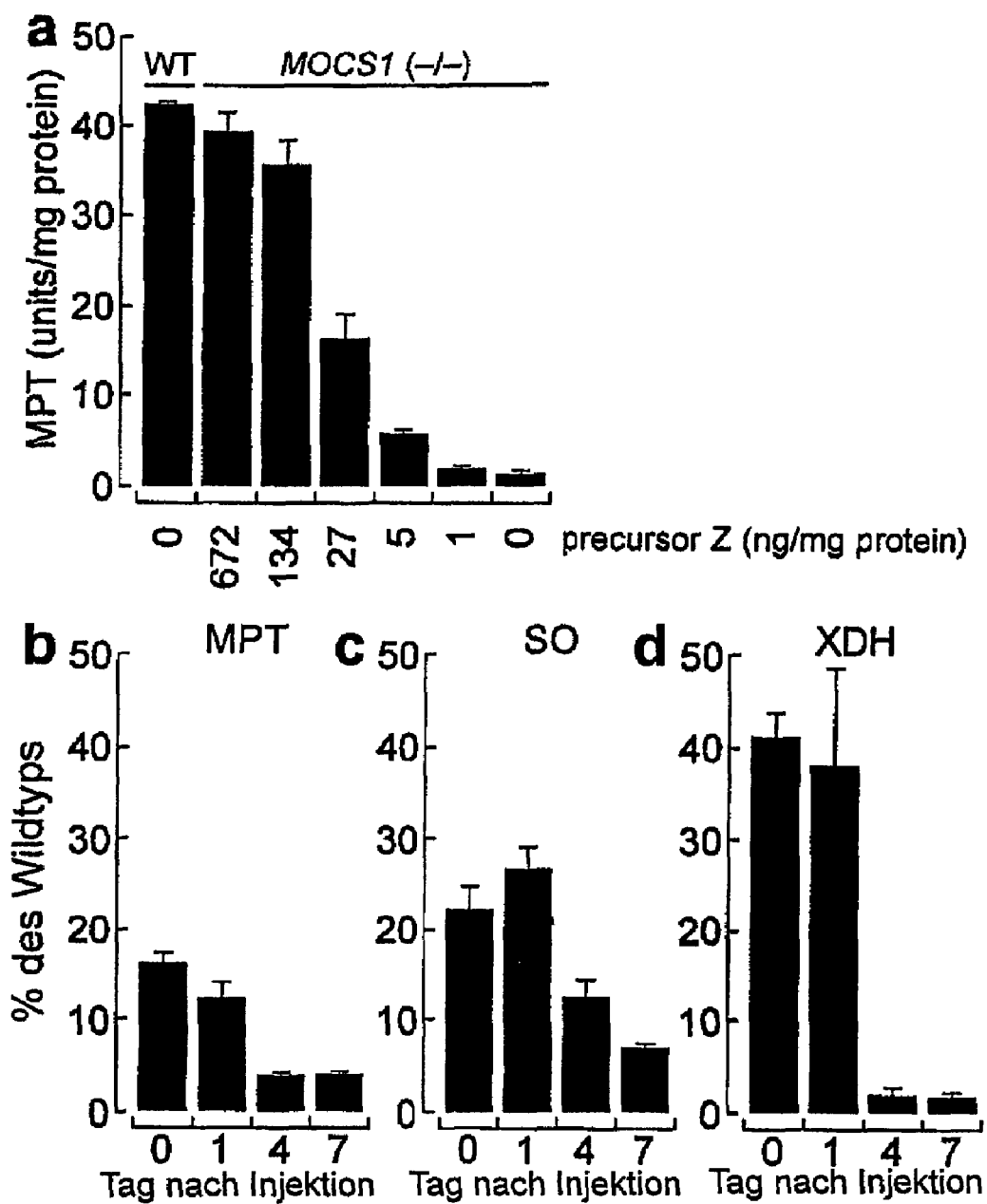

FIG. 6: Restoration of the MPT-biosynthesis in vitro and in vivo. (a) In vitro restoration of MOCS1-deficient liver extracts with precursor Z. Protein raw extract of a five day old MOCS1$^{-/-}$ were incubated (1 h) with the indicated amounts of purified precursor Z per mg protein. Restoration of MPT-synthesis was measured by means of nit-1 reconstitution assay. (b-d) Biochemical analysis of precursor Z treated MOCS1-deficient animals. The mice were twice weekly injected with increasing amounts of precursor Z, beginning with 2 μg after birth and up to 8 μg after weaning. Between the days 25-55 after birth the treatment was stopped. On day 0 (4 hours after the last injection), 1, 4 and 7 respectively, two mice were sacrificed. Two liver samples of each animal were removed and separately further processed. Each value in the figure was thus determined four times. Total-MPT inclusive Moco (b), sulphite oxidase activity (c) and xanthine dehydrogenase (d) are indicated as percentage of the corresponding wildtype value (n=4).

Figure 7:
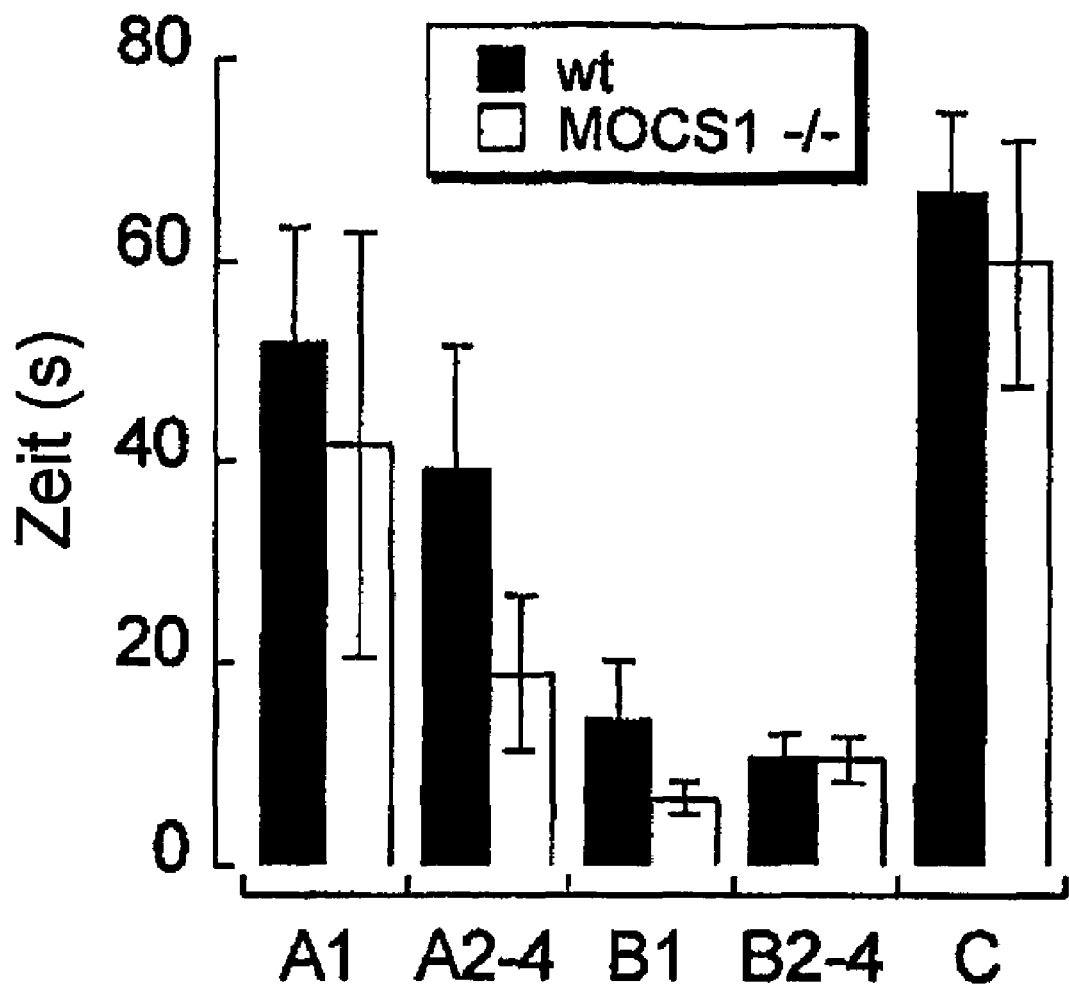

FIG. 7: Ability to train precursor Z-treated MOCS1-deficient mice in a water labyrinth. The values represented a cross section of six wildtype- (wt, black bars) and six precursor Z treated MOCS1-deficient mice (MOCS1 $^{-/-}$, white bars). The bars showed the time until finding the platform in the first attempt of the first pass (A1), the remaining three attempts of the first pass (A2-4), the first attempt of the second pass (B1) and finally the following three attempts of the second pass (B2-4). C, time (of a total of 120 seconds), spent in the correct sector (without platform), which were learned in passes A and B.

Figure 8:
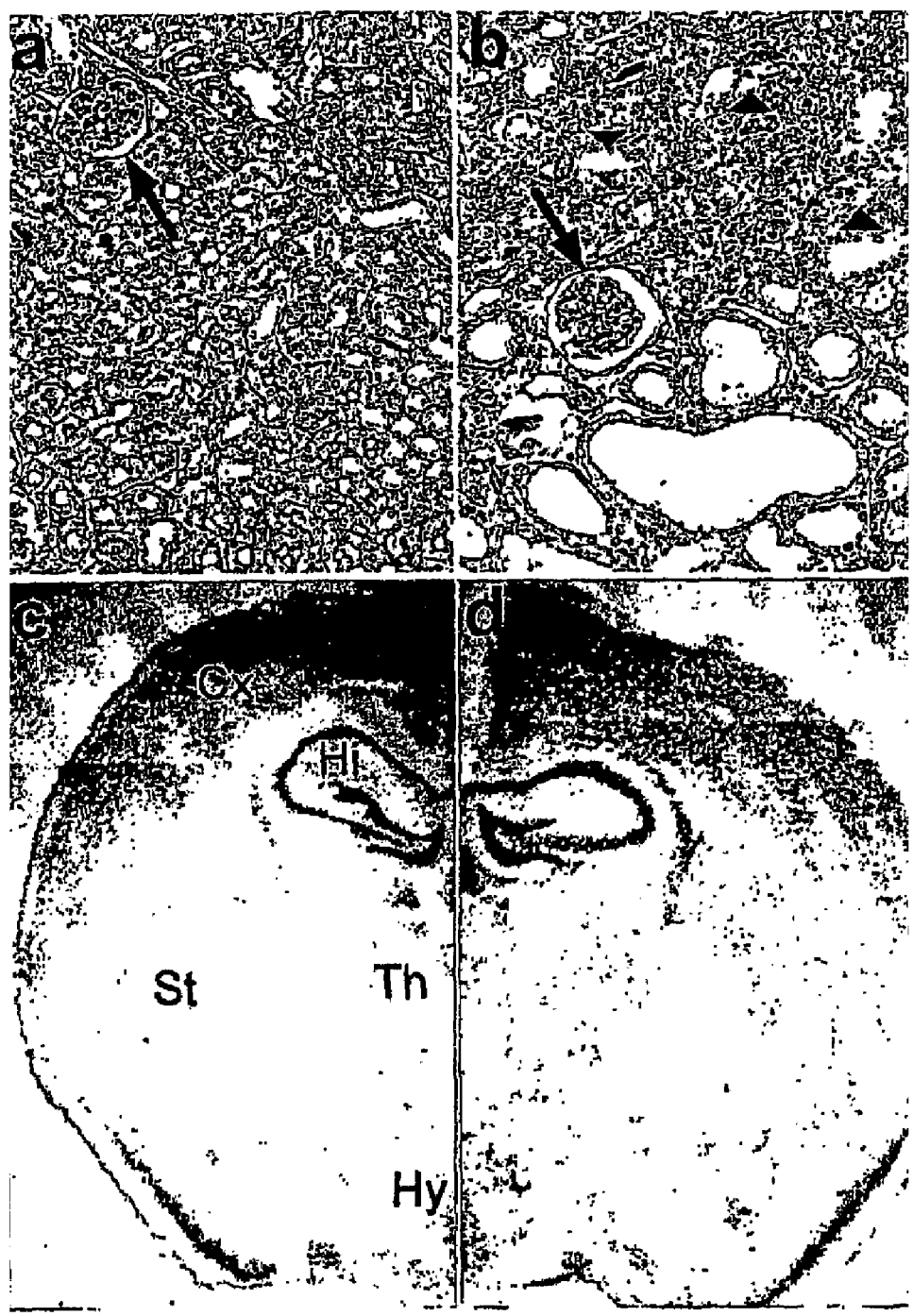

FIG. 8: Morphologic comparison of kidneys (a, b) and brain sections (c,d) of wildtype- (a,c) and precursor Z-treated MOCS1-deficient mice, (b,d). Treatment was with 2-4 μg each third day. (a) Regular kidneys with normal glomerulus (arrow), characteristic developed tubuli and thin (narrow) intersticies (200×). (b) In treated MOCS1-deficient mice, the kidneys developed numerous stones in the tubuli (□) with atrophied epithelia and formation of multi-grain giant cells (□). Proximal tubuli were extended (28+/−19%). The intersticies showed an enlargement of the matrix (13+/−13%) and a non-specific infiltration with single nuclei cells. The glomerulus is normal (arrow). (c,d) Corresponding coronal brain sections (Cx, Cortex; Hi, Hippocampus; Str, Striatum; Th, Thalamus; Hy, Hypothalamus) of wildtype-(c) and precursor Z-treated MOCS1$^{-/-}$ mice (d).

Spectroscopic Characterization and Structural Resolution of the Purified Precursor Z Highly resolution electrospray-ionization—mass spectrometry (ESI-MS) required a $[M+H]^+$-ion, which was compatible to the molecular formula $C_{10}H_{15}N_5O_8P$. Thereafter, the $^1$H-NMR-spectroscopy allowed not only the structurally characterization of the molecule, but rather confirmed also that this intermediate is subject to direct oxidation to already previously well-characterized, non-productive sequential product compound Z. The chemical $^1$H-shift and the data from the coupling constants do not agree with earlier structural models and indicate that precursor Z already exists as pyranopterin system as well as possesses a dual diol-functionality in the C1' position.

The molybdenum cofactor (Moco) is part of the active center of all Mo-dependent enzymes (1) with the exception of nitrogenase, and plays an important role in the global carbon, sulphur and nitrogen cycles (2). Mo-enzymes are essential for diverse metabolic processes such as for example detoxification of sulphur and purine catabolism in mammals (3) as well as nitrogen assimilation and phyto-hormone synthesis in plants (4). The Moco is comprised of an organic part, which originally was called molybdopterin (5), a pyranopterin with a terminal phosphate group, as well as a Mo-atom, which is bound via a ene-dithiol system (6). (FIG. 1). In all organisms examined until now, Moco was produced via an ancient and highly conserved synthesis pathway (7). In humans a mutation in any step of the Moco-biosynthesis in pleiotropes resulted in loss of activity of sulphite oxidase, aldehyde oxidase and xanthin oxidoidreductase (8, 9). Afflicted patients exhibited neurological abnormalities and died in early childhood, since until now no therapy was available (10). In addition to many prokaryotes, mainly archaea contained pyranopterin-ene-dithiolate cofactor similar to metal enzymes, which coordinates W in place of Mo. Thus, the fundamental pyranopterin component of Mo- and W-enzymes is abbreviated as MPT, which stands for MolybdoPTerin or Metal-binding Pyranopterin-DiThiol (11, 12). It is likewise presumed, that the W cofactor bisynthesis of Moco-biosynthesis is similar, with the exception of the final step of the metal insertion (7).

The Moco-biosynthesis (FIG. 1) can be sub-divided into three steps (7, 13). First the sulphur free precursor Z is synthesized from a guanosine derivative by the action of two proteins (14, 15). In the second step, precursor Z is converted by the insertion of two sulphur atoms at the C1' and C2' positions, converted to MPT (see new numbering in FIG. 1), whereby an ene-dithiol-function is formed (16). This reaction is catalyzed by the heterotetramer MPT-snythase (17), which convey to sulphur atoms from two thicarboxylated small sub-units to the carbon atoms C1' and C2'. In the later step of the Moco-biosynthesis a Mo-atom is transferred to one (pro- and eucaryotic) or two (prokaryotic) MPT-dithiol end groups, which leads to the formation of Moco (20, 21). In the bacteria, a supplemental modification of the pterinphosphate by attachment or pendency of a nucleotide was observed (22). The fundamental chemical structure of Moco was resolved by the pioneering research of Rajagopalan and colleagues (13, 23). Their latest description of Moco was resolved with crystal structures of Mo (24) and W-containing enzymes (25), in which a not previously seen supplemental pyranoring was discovered, which is formed between the hydroxyl groups of the C3'-atoms and C7-position of the pterins (FIG. 1). Based upon this observation, it was presumed, that the pyranoring was either already present in the intermediates (12, 18, 26), or that it was formed during the insertion in the Apoenzyme (27). Until now neither MPT nor precursor Z were examined by means of $^1$H- or $^{13}$C-NMR-spectroscopy or crystalized. Thus, the question remained open, as to whether or not the pterin side chain formed a pyranopterin structure already in an earlier step of the Moco biosynthesis.

The structural model of precursor Z was based upon the structure of the oxidation product (28), on $^{31}$P-NMR-spectroscopy, on mass spectrometry (MS) as well as oxidation studies (14). The direct stoichiometric conversion of precursor Z via a two-electron oxidation to stable oxidation product compound Z implicated a dihydro condition of precursor Z, which was explained by a chinonoide structure and an enol-function in C1', which could be subject to a keto-enol toutomerisation (14). Precursor Z, just like compound Z, is sulphur free and contains a cyclic phosphate, which bonds C2' and C4'. In comparison to MPT and Moco, precursor Z is the stablized intermediate with an estimated half time of several hours at low pH-values (14).

For this reason a method for the purification of large amounts of precursor Z from E. coli was established. We report on a detailed spectroscopic analysis and structural characterization of precursor Z. By $^1$H-NMR and MS-methods, we show that precursor Z already has a completely reduced pyranopterin structure and is hydrated primarily on the C1' position, which leads to a dual diol.

Chemicals

NaCl, yeast, trypton and isopropyl thiogalactoside was obtained from Duchefa Biochemie, ammonium acetate was obtained from Merck, citric acid monohydrate and sodium citrate dihydrate were obtained from Baker, formic acid was obtained from Sigma, $D_2O$ and DCl were obtained from Deutero GmbH and NaOD was obtained from Fluka AG.

Construction of the Plasmid for Coexpression of MoaA and MoaC.

E. coli moaA and moaC were cloned from pJR11 using PCR (29). The published gene sequence (30) was used for the production of oligoneuclutides, which made possible cloning in the Nde I- and Xho I-clevage sites of the cloning region of the pET15b-expression vector (Novagen). The plasmids produced were named pPh15moA and pPH15moaC. The complete moaC-expression unit inclusive of the IPTG-regulated T7-promotor/operator element and the synthesis ribosome-bonding site of pPH 15moaA were subsequently sub-cloned in the Sph I- and Hind III-clevage sites of pLyssS (Novagen), from which the pPHLysmoaC resulted.

Isolation and Purification of Precursor Z

Precursor Z was purified from E. coli by means of a modified protocol, which has already been described (14). MJ7 clM (DE3)-cells (31), which were contained in the pasmides pPh15moaA and pPHLysmoaC were cultured anaerobically at 20° C. in LB-medium with 120 μg/ml Ampicillin, 30 μg/ml Chloramphenicol and 50 μM IPTG and harvested by means of centrifugation (5 min, 12,000 g, 4° C.). Prior to the HPLC-purification, the cells were resuspended in two volumes 0.4 M HCl, sonicated and centifuged. In order to detect any possible modifications, which could result from the acidification of the cells, the cells were extracted in a controlled experiment in 100 mM acetate-buffer (pH 3.0). The clear supernatant was introduced to a semi-preparative "Reversed-Phase"-column (C8, 5 μm, 250*10 mm, Kromasil, EKA Chemicals), which was equalibrated in 5 mM ammonium acetate, pH 5.0. Precursor Z was eluted in the first absorption maximum and was immediately frozen in liquid nitrogen. In the second step the precursor Z containing fractions were purified and introduced on a semi-preparative SAX-column (15 μm, 250×10 mm, Adsorptionsphere, Alltech), which was equalibrated in 10 mM citrate buffer (ph 3.0). Precursor Z was elutted isocratically after approximately 30 ml and frozen in liquid nitrogen. A subsequent purification was achieved by the application of precursor Z on an analytic "reversed-Phase"-column (C18, 5 μm, 250×4 mm, Alltech), equilibrated in 10 mM formic acid. precursor Z containing fractions were combined, frozen in 20 μl aliquots in liquid nitrogen and stored until further use at −80° C. Concentrations of precursor Z were determinedat an extinction coefficient $\square_{267\,nm}$=8960 M cm$^{-1}$ (14).

Electrospray Mass Spectrometry

Precursor Z was dissolved in a 1:1 (vol:vol) methanol/1% formic acid mixture. Approximately 3 µl of this solution (final concentration approximately 20 pmol/µl) were introduced into a gold-coated nonospray capillary. The tip of the capillary was placed vertically in front of the inlet opening of a "quadrupole-time-of-flight" (QTOF 2)-mass spectrometer (Micromass), which was equipped with a nanospray-ion source, and a voltage of 1000 V was applied. For collision-induced dissociation experiments parental ions were selectively transmitted from the qudrupol-mass analyzer into the collision cell. As collision gas, argon was used, and the kenetic energy was set to approximately −25 eV. The resulting sister ions were subsequently separated by orthogonal "time-of-flight"-mass analyzer. The isotopic composition of the sample was determined in the accurate mass mode, which employed reserpin ([M+H]$^+$=609.2811 Da) as internal reference molecule.

$^1$H-NMR—Spectroscopy

One- (1D) and two-dimensional (2D) $^1$H-NMR-correlation spectra (COSY) were recorded at 300 K with a Bruker Avance DMX 600 NMR-spectrometer, which is linked to the dominating resonance of deuterium from the solvent D$_2$O. Chemical shifts are indicated in ppm relative to the background signal of the solvent (4.80 ppm) and couplings in Hz. Precursor Z containing samples (100-200 µg) were freeze-dried and resuspended in 700 µl degassed D$_2$O and 2 µl 36% DCl. For avoidance of oxidation, the pipette was gased for 5 minuites with nitrogen. These solutions were stable enough for recording both 1D- and 2D-COSY-spectra. Subsequent exposure of the solution to air caused the oxidation of the precursor Z to the well-described main single product, compound Z, and this reaction was monitored at regular intervals by recording 1D-$^1$H-spectra. Under normal conditions, this reaction is concluded after 14 days in D$_2$O and DCl.

Results

Isolation and Purification of Precursor Z

Precursor Z was isolated from *E. coli* and purified in a three-stap HPLC-chromotographic procedure, via which a homogonous product was produced, which was verified by UV-Vis-(data not shown), ESI-MS- and $^1$H-NMR-spectroscopy (see below). On average, a yield of 40 µg precursor Z pro liter *E. coli* culture was achieved. The isolated molecule was identical with earlier preparations (12), since it exhibited the same UV-Vis-Absorption spectrum with an absorption maximum at 267 nm at pH 3.0 and after exposure to air had the same, unique characterized oxidation product, compound Z, as result.

ESI-MS of Precursor Z

Figure 2A:
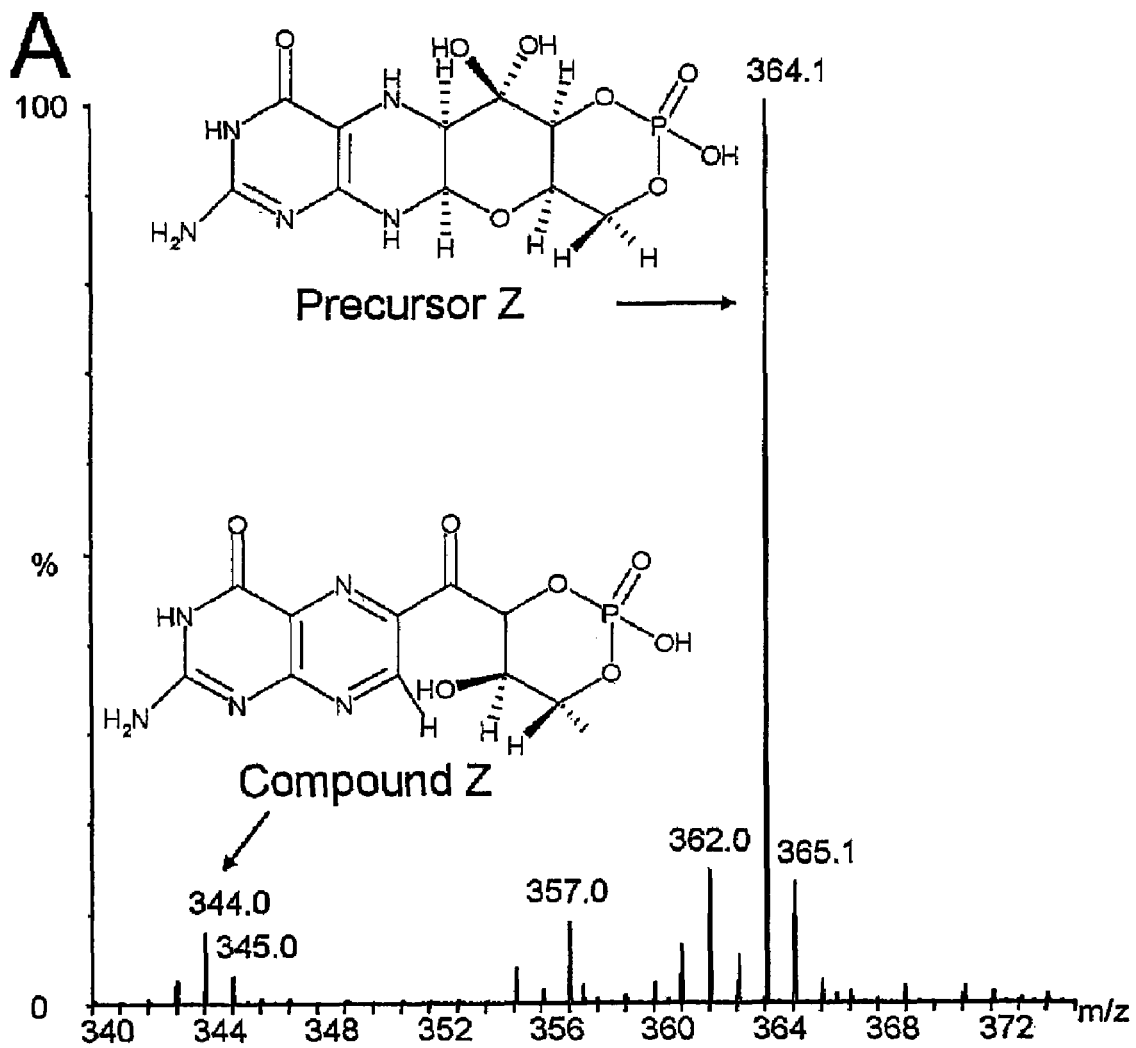
Figure 2B:
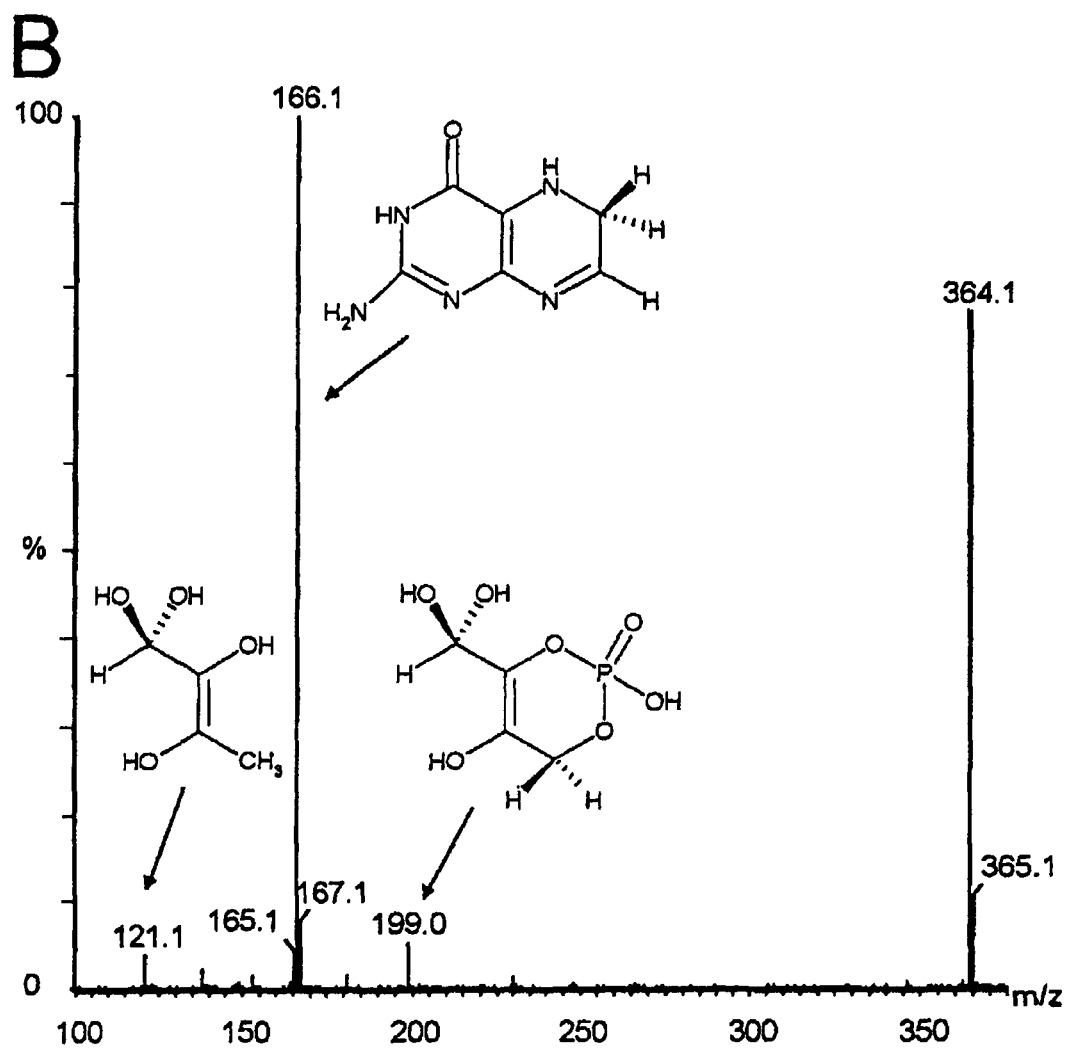

ESI-MS was employed, in order to determine the molecular mass of precursor Z. In positive ion mode, the ESI-MS produced a [M+H]$^+$ ion at 364 Da (FIG. 2A), wich was 18 Da larger than the expected mass of 346 Da of the earlier molecular structure (14). In fact, there was no indication of such a peak in the spectrum. An additional smaller peak in the spectrum (FIG. 2A) at 344 Da corresponded to the expected mass for compound Z (14), which is unavoidably present in such samples due to partial oxidation (FIG. 2A). This fact was also confirmed by $^1$H-NMR-analysis (see below). In contrast to earlier attempts with thermospray or "fast atom bombardment ionization", we were able to determine a precise mass for precursor Z in positive ion mode by means of ESI-MS with 364.064±0.003 Da (364.0658 Da computed for $C_{10}H_{15}N_5O_8P$). In accordance with the molecular formula of precursor Z $C_{10}H_{14}N_5O_8P$, which did not correspond with the earlier postulated formula $C_{10}H_{12}N_5O_7P$ (12). The new formula of the 364 Da-peak allowed a presumption of a hydration of precursor Z, which likely occurs at the C1'-position for which a single hydroxyation function with a possible keto-enol-tautomeriaztion had already been proposed (14). The supplemental hydration at C1' would then result in the formation of a dual diol (FIG. 2A). A MS/MS of the 364 Da-peak showed a main fragment at 166 Da (FIG. 2B), which corresponded to a semi-oxidized dihydropterin and hinted towards the pterin nature of the peak. The dihydropterin can then simply be formed following the opening of the pyranoring without further oxidation (compare with Moco in FIG. 1). Two additional peaks were observed at 121 Da and 199 Da, which respectively corresonded to the masses of the side chains without, or, as the case may be, with, the cyclic phosphate. Both masses correlated only to the hydrated side chain fragment, which possessed a dual diol in the C1' position. Besides this, the MS/MS of the 344 Da-peak produced, in the rear sample or in the sample of purified compound Z, a similar sister ion spectrum with a dominating fragment at 164 Da (data not shown), which correspondes to a completely oxidized non-substituted pterin which is comparable with the MS/MS-data of other hydrogenated pterins (32).

$^1$H-NMR—Spectroscopy of Precursor Z

In order to resolve the structure of the precursor Z and to confirm our hypothesis regarding the hydration, which was observed in the MS, we recorded $^1$H-NMR-spectra in acidified D$_2$O and followed the changes of the signal positions and intensities during the oxidation to compound Z (FIG. 3A-D). On the basis of the $^1$H chemical shifts (FIG. 3A-C), the compounds of the 2D COSY-spectra (FIG. 3D), and the magnitudes of the coupling constants, all expected signals (six protons, H$_a$-H$_f$) were could be clearly assigned (Table 1). The $^1$H chemical shift and coupling constants ($^1$H-$^1$H and $^{31}$P-$^1$H) of the oxidation product compound Z were comparable with the published data (15, 28) and identified these without doubt as compound Z (FIG. 3C). The three $^1$H-NMR-signals of the protons H$_a$, H$_b$ and H$_c$ in precursor Z, with regard to the chemical shifts, as well as the $^1$H-$^1$H and $^1$H-$^{31}$P coupling constants (FIG. 3 and Table 1), are comparable with the protons that are present in the spectrum of compound Z (H$_a$', H$_b$', and H$_c$'). These three protons were assigned C4' (Ha and Hb) and C3' (H$_3$), and the magnitude of the adjacent 1H-31P-couplings of the C4' protons (22.7 or, as the case may be, 2.1 Hz) indicated the intact cyclic phosphate (12). The largest shift of H$_c$ among these three protons indicated significant changes in the environment of C3', which could be explained by the opening of the opposed pyranopterin-ring structure in precursor Z during the oxidation to compound Z. The signal of the remaining three protons (H$_d$, H$_e$ and H$_f$) of precursor Z deviated significantly from those of compound Z (H$_d$', H$_e$', and H$_f$', FIG. 3 and Table 1). Precursor Z showed a 1.7 Hz-doublet at 5.39 ppm (H$_f$), which correlated with the broad doublet (broad signal) at 3.62 ppm (He) These two signals eventually became lost during the conversion to compound Z, while at the same time the signal appears at 9.39 ppm (H$_f$, FIG. 3A-C). The chemical shift of H$_f$- and H$_e$-signals is comparable with the seldom chemically synthesized pyranopterin (33). Independent of the highly resolved ESI-MS-data, the coupling constants indicate a larger difference in the chemical shift of these two protons compared to the earlier structural model, since they had belonged to a nitrogen-substituted methyl group. The third important signal indicates similar adjacent couplings to H$_c$ and P both in precursor Z as well as in compound Z, however, shifts during the oxidation process dropped downwards from 4.415 ppm to 6.32 ppm (FIG. 3 and Table 1). These data implicate the same relative arrangement of $H_d$ in comparison to $H_c$ and P in both compounds. The 1.87 ppm difference in the chemical shift or shift of the Hd signal favors rather a significant change in substituents at C1' between precursor Z and compound Z, whereby the possibility of an unchanged Keto function in both compounds is excluded. Supplemental $^1$H-NMR-spectra were recorded at different pH-values (1, 3, 7 and 10) without significant changes to be observed in the proton signals of precursor Z (data not shown). The sole noteable difference at higher pH-values was the broadening of the $H_e$ and $H_f$ signals, which can be associated with a more rapid oxidation to compound Z therewith the high resolution ESI-MS- and $^1$H-NMR-data for precursor Z together with the observed changes in the oxidation to compound are compatible only with the closed pyranopterin structure and a diol in C1' (FIG. 4E).

TABLE 1

$^1$H-NMR-Signals of precursor Z and compound Z at pH 1 in $D_2O/DCl$.

| $^1$H-Signals | Chemical Shifts (ppm)* | Coupling Constant $(H_Z)$ J ($^1$H-$^1$H,$^{31}$P-$^1$H) | COSY |
|---|---|---|---|
| | | precursor Z | |
| $H_a$ | 4.41(ddd) | 22.7($^{31}$P), 13($H_b$), 1.9($H_c$) | $H_b$, $H_c$ |
| $H_b$ | 4.51(dt) | 13($H_a$), 2.1($^{31}$P), 2.0($H_c$) | $H_a$, $H_c$ |
| $H_c$ | 4.12(q)(br) | 1.9($H_a$), 1.9($H_b$), 1.9($^{31}$P), 1.9($H_d$) | $H_a$, $H_b$, $H_d$ |
| $H_d$ | 4.45(t)(br) | 1.6($^{31}$P), 1.6($H_c$), ~0.8($H_e$) | $H_c$, $H_e$ |
| $H_e$ | 3.62(d)(br) | ~1.7($H_f$), ~0.8($H_d$) | $H_f$, $H_d$ |
| $H_f$ | 5.39(d) | 1.7($H_e$) | $H_e$ |
| | | compound Z | |
| $H_a'$ | 4.26(ddd) | 22.7($^{31}$P), 12.5($H_b$), 1.9($H_c$) | $H_b$, $H_c$ |
| $H_b'$ | 4.80(dt) 4.97(dt) at 315 K | 12.5($H_a$), 1.9($^{31}$P), 1.9($H_c$) | $H_a$, $H_c$ |
| $H_c'$ | 4.64(q) | 1.9($H_a$), 1.9($H_b$), 1.9($^{31}$P), 1.9($H_d$) | $H_a$, $H_b$, $H_d$ |
| $H_d'$ | 6.32(t) | 1.6($^{31}$P), 1.6($H_c$) | $H_c$ |
| $H_e'$ | — | — | — |
| $H_f'$ | 9.39(s) | — | — |

*Chemical Shifts recorded at 300 K, unless otherwise indicated. Coupling constants are indicated in brackets: s = Singlet, d = Dublett, t = Triplett, q = Quintett. Broad Peaks are indicated with (br).

Discussion

Precursor Z was first identified by Wuebbens and Rajagopalan (14) and described as a dihydropterin-structure with a C6-substituted four-carbon side chain as well as a hydroxyl function in C1'. Based upon the dihydro condition and the relative stability of the precursor Z, a chinonide structure of precursor Z was postulated with a possible keto-enol-tautomerisation in the C1' position (14). New insights into the structure Moco were derived from the crystal structures of the Mo-enzyme (24, 34, 35) and raised the question whether a non-coordinated MPT and/or precursor Z already possessed a pyranopterin structure (12). In the here postulated study we have addressed this question and have described and verified the side chain structure of precursor Z by the use of MS and $^1$H-NMR-spectrascopy using sufficient amounts of purified precursor Z. It was the goal of this study to establish the oxidation condition of the precursor Z pterin system, in order to explain its role in connection with biosynthesis pathway. The observation of two protons at C6(He) and C7(Hf), which showed an adjacent coupling of 1.7 Hz (COSY) and a large chemical shift difference, implicated, that precursor Z was completely hydrated in the pyrazine ring of the pterin. A dihydropterin would have required a double bond either between N5 and C6(7,8-dihydro), C6and C7(5,8-dihydro) or N8 and C7(5,6-dihydro). In the case of 7,8- or 5,8-dihydropterin, the He-proton would be lost, while for the 5,6-dihydropterin the presence of a double bond between C7 and N8 would lead, due to the pull back effect of the double bond, as has already been observed in other dihydropterin (36), in a substantial shift to a low field resonance of the $H_f$-signal (~7.5 ppm). Further, the chemical shift difference between both pterin protons ($H_e$ and $H_f$) of 1.77 ppm is very similar to those, which were described in the few reports regarding chemical synthesized pyranopterin ($H_e$=1,3 ppm, $H_f$=4.8 ppm in DMSO) (33). Likewise, it was important to determine whether there was a double bond between C1' and C2', as weas found in MPT and Moco. The presence of the precursor Z signal at 4.41 ppm (Hd), which displayed the same coupling partner as in compound Z, allowed the association of the proton at the C2'-position. According thererto, the presence of protons at C2' and C6 exclude the presence of a double bond formation either between C6 and C1' (14) or C1' and C2' (26). Since the $^1$H-NMR-data do not suggest the presence of a proton at C1', it would be possible that a carbonyl group is position at C1'; comparable with that in compound Z (15, 28). Both the high resolution ESI-MS-mass spectrum of precursor Z as well as the large difference in the chemical shift (1.87 ppm) for the C2'-bound Hd proton between precursor Z and compound Z could not be explained with the aromatisation of the pterin ring exclusively by the oxidation to compound Z, but rather requires supplementally a change in the substitutants at C1' by the formation of a duo diol. Since all $^1$H-NMR and ESI-MS-spectra were recorded in acidic pH-values of 1-3, the dual diol could be the product of an in vitro hydration, which is catalysed under acidic conditions. In order to determine whether a carbonyl group is formed under various pH-conditions in an equalibrium reaction, 1H-NMR-spectra were recorded at different pH-values (1-10). The single difference observed in the spectra was a broadening of the signal of $H_e$ and $H_f$, while $H_d$ showed no change. From this we could conclude, that the dual diol was the main product in all pH-values. Hydration at the C1' position of the side chain appeared to be a common characteristic in tetrahydropterin, since in the intermediate (6-pyruvoyl-5, 6, 7, 8-tetrahydropterin) in the biosynthesis of tetrahydropterin a dual diol at the C1' position with more than 90% hydroxylation at neutral pH could be verified (37). Besides a hyration in vitro, the possibility of an in vivo-hydration during the synthesis of precursor Z could exist. From this we conclude that the dual diol in precursor Z and other reduced pterins could serve as a protective function. Until now the theories constructed for the mechanism of the precursor Z biosynthesis (15, 38, 39) neither took into consideration the formation of a dual diol nor the synthesis of a pyranopterin. It was postulated, that the precursor Z formation proceeds with guanosine-derivative as starting component (14, 15). During precursor Z biosynthesis, all carbon atoms of the guanosine were used, while the imidazolring-C8-atom was maintained and in a conversion reaction was incorporated in precursor Z as C1' (14, 15). For this reaction the formation of a transient formylester is discussed (15), which could be bound to the conserved and functionally important C-terminus of proteins of the MOCS1A-family (40). The dual diol could be the product of the formyl release reaction during the precursor Z synthesis. Besides the elevated stability the dual diol could possess a second biosynthetic function. We have shown, that *E. coli* MPT-synthase transmits two sulphur atoms from two different phytocarboxyated small impurities to precursor Z, which suggests the formation of a single sulphur intermediate (18), of which the existence has recently been shown (26). The transmission of the first sulphur atom accompanies the opening of the cyclic phosphate, which indicates the initial attack at the C2'-position. The latter makes sense with regard to the low reactivity of the dual diol at C1' compared with a keto functionality. The second step of the reaction would involve the release of both hydroxyl groups as well as the transferrence of the second sulphur atom.

In summary, we conclude that the basic structure of precursor Z is a pyranopterin. This discovery shows that not only the Moco but rather also both intermediates of the biosynthetic pathway (precursor Z and MPT) exist as pyranopterin and that the opening of this pyrano ring feature would with high probability irreverisbly destroy all intermediate products inclusive of Moco itself. Both the pyrano ring formation as well as the observed dual diol functionality in C1' appears to be important, in order to (i) protect precursor Z from oxidation, (ii) to maintain the stereo chemistry of the pterin-C6-position and (iii) to ensure the directed reactivity of precursor Z during the MPT-synthesis.

Healing of Deadly Molybdenum-Cofactor-Deficiency by a Biosynthetic Precursor of *Escherichia coli*

We have recently described the construction of an animal model for human Moco-deficiency Type $A^{B25}$. These MOCS1 knock-out mice exhibit a severe phenotype, which corresponds with the biochemical characteristics of human Moco-deficiency patients. The mice are inhibited in growth and die within the first 12 days following birth, with an average life span of 7.5 days.

This lethal phenotype can inventively be rectified by a biosynthetic intermediate precursor Z from *E. coli*, effectively.

Results

Purification and Stability of Precursor Z

Precursor Z was purified to homogenity by a three step process, including HPLC chromatography (FIG. 4), which could be demonstrated both by means of UV-VIS spectroscopy (FIG. 5b) as well as on the basis of mass spectrometry (data not shown). In order to obtain larger amounts, we used a bacterial strain, which enriched precursor Z on the basis of a defect in the conversion to MPT. A further improvement in the yield could be achieved by over expression of the protein MoaA and MoaC, which catalyse the first step of Mocosynthesis. This leads to an approximately 5000-fold enrichment of precursor Z in comparison to wild type cells, with an average yield of 40 μg per L *E. coli* culture and a final concentration of 30-140 μg/ml. Purified precursor Z showed the same absorption spectrum as previously described$^{B19}$ and could qualitatively be oxidized to compound Z (FIGS. 5a, b). Under physiological and aerobic conditions at pH 6.9 (2×PBS buffer) a 22 μM solution of precursor Z was oxidized within 5 h completely to compound $ZBe^9$. The halftime of precursor Z at pH 6.9 could be determined with 62±12 (FIG. 5c).

Reestablishment of MPT-Biosynthesis In Vitro

The biological activity of the purified precursor Z could be verified by a quantitive in vitro conversion to MPT tinder use of purified *E. coli* MPT-Synthase$^B$26. With a double excess of MPT-synthase we were able to almost completely convert precursor Z into MPT, which was determined HPLC formA analysis (data not shown). In order to determine the amount of precursor Z needed for a successful reestablishment of Moco-biosynthesis in MOCS1-deficient mice, we carried out an in vitro reconstitution with various amount of precursor Z in protein-raw extract from the liver of five day old MOCS1-deficient mice carried out (FIG. 6a). In the case of the employment of 134 ng precursor Z/mg protein a near complete reestablishment of Moco-biosynthesis could be achieved, while 27 ng precursor Z led to a reconstitution of approximately 50%. The protein total concentration of the liver extract amounted to 6 mg (obtained from 50 mg total liver tissue) which necessitated a total required amount of precursor Z of 0.8 μg for each animal for complete reestablishment of the MPT-synthesis under in vitro conditions. Accordingly for an adult animal with a body weight of 20 g and an approximate mass or weight of the liver of 1 g, 16 μg precursor Z was needed for complete reestablishment, however only 3 μg for an activation of 50%. Since the production availability for precursor Z was limited, we did not attempt in the following experiments, to achieve a complete reestablishment, but rather only used the minimal necessary dose. Although the in vitro titration experiment yielded no information regarding which part of the Moco is transmitted to the Apo-sulfhite-oxidase, the investigated or established amount of precursor Z related to the maximal capacity of the MPT-production in the liver of MOCS1-deficient mice.

Healing of the Lethal Phenal Type in Moco-Deficient Mice

It could be reliably demonstrated that the loss of the sulphite oxidase activity was exclusively responsible for the severe neurological damage that occurs as consequence of Moco-deficiency$^{B11}$. The half-life of sulphite oxidase in rat liver was determined to be 3-4 days$^B$27. On this basis of the above-described calculations, we injected precursor Z into the liver, as summarized in Table 2. Although untreated homozygous animals, in comparison to their type siblings of the same litter, gained weight significantly slower and died very early$^{B25}$, it was impossible to visually identify treated homozygote animals in a single litter without determining the genotype. With regard to the weight, behavior or other phenotypic characteristics no difference could be determined between precursor Z-treated MOCS1-deficient mice and wild type, or as the case may be heteroxyled siblings of a single litter prior to weaning.

TABLE 2

Lifespan of MOCS1 —/— Mice with Different Treatments

| Treatment$^a$ | n | Average Lifespan (Days) |
| --- | --- | --- |
| Untreated$^b$ | 28 | 75 |
| 0.2 μg every second day | 11 | 17.7 |
| 1 μg every third day | 5 | 25.2 |
| 1 μg (prior to weaning$^c$) and 2 μg (after weaning) every third day | 30 | 32.9 |
| 2 μg precursor Z every second day | 15 | 47.4 |
| 2 μg (prior to weaning) und 4 μg (after weaning) every third day | 18 | 91.,8 |

$^a$Precursor Z was injected through the skin into the liver.
$^b$Data from source B16.
$^c$Weaning occurred between day 20 and 30 after birth.

As can be seen from Table 2, there is a strong correlation between the amount of precursor Z injected per week and the average life span of the MOCS1-deficient mice. The lowest dose amounted to 0.2 μg precursor Z, administered every second day. With this treatment 11 MOCS1$^{-/-}$ mice from three litters developed normally and gained weight corresponding to their cospecifics. Although no difference could be determined in behavior, all 11 homozygote animals were selectively killed by their parents between days 14 and 19. With the administration of 1-2 μg every third day the mice achieved a greater age and were suckled until day 20-30, thereafter the MOCS1$^{-/-}$ animals however appeared slower in their flight reaction and in their internalization of their environment than the corresponding control animals. This difference disappeared about day 40, after which all MOCS1$^{-/-}$ animals were as agile and full of life as the control individuals. Approximately half of the treated animals died between day 20 and 40. The injection of 2-4 μg precursor Z every third day ws found to be the most successful treatment. During this treatment no animal died between days 40-70, a span in time in which males and females reach adult stage and reproductive ability. Ten pairs of these treated animals among themselves and four additional MOCS1-heterozygotes (two pairings with homozygote males and two with homozygote females) produced normally developed, healthy off-spring, which in the case of the MOCS1$^{-/-}$ phenotype had again to be treated with precursor Z.

Prevention of Neurological Damage

The overall activity of the treated animals (214 μg precursor Z every third day) was determined in "open field" test, wherein the examined parameters (movement, learning and social behavior) produced no significant differences between wildtype (n=6) and homozygous animals (n=8) of a single litter. Avoidance of light was tested in the light/dark box, in which the animals were placed into the light area and the time was determined until the animals sought out the darker area. This test also produced no significant difference between wild type and MOCS1-deficient, precursor Z treated mice (data not shown). Limitations of movement were not shown for the MOCS1-deficient and precursor Z treated mice in a running wheel test (10 and 20 RPM, data not shown). The ability of the MOCS1-deficient mice, which regularly were administered precursor Z, to learn was determined in a four sector subdivided water labyrinth, which had a non-visible platform in one sector. The results were compared with wildtype controls. The mice were sequentially introduced into all four sectors and the time was measured until the animals found and climbed onto the platform (FIG. 7). In the first series of tests, the treated "knockout" mice (n=6) found the platform more rapidly than the wild-type control animals (n=6). In a second test series, the average swim time was reduced to 20-25% of the first test both in the "knockout" mice as well as with the control animals. In a third test series, the platform was removed and the time was measured that the mice spent in the "correct" sector—the sector that previously contained the platform. Both groups spent approximately 50% of the time in the correct sector.

The Reoccurrence of Deficient Phenotype After Cessation of Treatment

In order to test whether the treatment with precursor Z can be halted after a certain developmental stage, we stopped the injection of precursor Z in homozygouse mutants on days 1 (n=3), 12 (n=4), 26-28 (n=3) and 64-68 (n=2) after birth. A single injection of precursor Z after day one led to death after 15-18 days. The cessation of precursor Z on day 12 resulted in limited exploration of the environment, beginning on day 18 (that is, 6 days after the last injection), and death of the animals 1-3 days later (that is 7-9 days after the last injection). At the age of 26-28 days, in which the previously described critical period falls, the cessation of administration of precursor Z led to death within 4-7 days. Cessation after 64-68 days led to reduced exploration of the environment after 7 days and to death after 9-10 days. In order to successfully correct the phenotype, the administration with precursor Z had to be initiated within 5 days following birth. A initiation of treatment after 7 or, as the case may be, 10 days led to no significant improvement of the phenotype or the life expectancy (data not shown).

Reestablishment of Moco-Synthis and Moco-Dependent Enzyme Activities In Vivo

In homozygote MOCS1$^{-/-}$-animals, in which precursor Z was injected regularly and which appeared normal with regard to weight, appearance and behavior, the treatment was halted and the animals were sacrificed sequentially at days 0, 1, 4 and 7 after the last injection in order to determine the MPT-content and the Mo-enzyme activity in the liver (FIG. 6b-d). Due to the rapid conversion of the administered precursor Z to MPT, the highest MPT-value was measured on the day of the injection (16±1% of the wildtype; FIG. 6b). Within the following four days the MPT-content fell continuously to less than 4% of the wildtype value.

The activity of the sulphite oxidase showed a rise from day 0 to day 1 after the last injection (FIG. 6c). Both sulphite oxidase as well as xanthin-dehydrogenase-activity achieved a relevant value (indicated in % of wildtype), which was higher than the reconstituted MPT-content (FIG. 6d). After day 1 the xanthin dehydrogenaseactivity rapidly decreased. Morphologic examination of precursor Z treated knockout mice produced bilateral abnormal kidneys beginning day 20 after birth (FIGS. 8a, b). This correlates with the very high value of xanthin as well as not measurable values of uric acid in the urine (data not shown). Besides kidney damage, no further morphologic abnormality was observed. Tissue from heart, skeletal muscle, lung, pancreas, thyroid, spleen and liver (data not shown) as well as brain (FIG. 8c-d) were examined.

Discussion

The reestablishment of mouse Moco-biosynthesis by bacterial precursor Z in vivo and in vitro supports the genetic indication of a unique and highly conserved synthesis pathway, which leads to Moco and Moco-dependent enzyme activity[12]. We observed a clear correlation between the routinely administered amount of precursor Z and the life expectancy of MOCS1-deficient mice (Table 2). The selective termination of the concerned offspring by the parents following the lowest dose administered here could indicate either a different smell—possibly caused by elevated values of sulphur containing compounds—or slight changes in social behavior. The high mortality between day 20-40 after birth, which occurred following treatment with average amount of precursor Z (1-2 μg) and cessation of treatment, could be caused by the critical phase in the brain development, since these animals react very sensitive to elevated sulphite or as the case may be reduced sulphate concentrations. In the case of high dosing the activity of the sulphite oxidase in the liver increases in the first days of injection of precursor Z, which indicates, (i) the apoenzyme which takes up Moco is less stable than the holoenzyme, (ii) the available apoenzyme molecule is rapidly saturated with Moco and (iii) apoenzyme must be newly synthesized, in order to take up all available Moco. Compared with the wildtype value both the activity of the sulphite oxidase as well as the xanthin-dehydrogenase exceeds the percentage of re-established MPT (FIG. 6). This insight allows us to conclude a very efficient incorporation of available Moco in the Apoenzyme as well as to a fraction of Moco in the wildtype, which is not bound to the Mocoenzyme. Beyond this, this insight agrees with earlier observations regarding gephyrin-deficient cell lines, wherein minimal amounts of reconstituted Moco led to a over proportionally high activity of the suphite-oxidase[B22].

To the extent that we are aware, the stability of xanthindeydrogenase in vivo has until now has not been determined, however the half life of the associated mRNA has been estimated 12-16 hours$^{B28}$, which represents the magnitude of the half life of the enzyme activity, which was estimated on a basis of the differences between day 1 and day 4 after precursor Z injection (FIG. 6d). The activity of the sulphite oxidase, after achieving a maximum at day 1, adheres to the published half life of 3-4 days$^{B}$27 (FIG. 6c). Possibly the average activity of the xanthin-dehydrogenase is lower than the activity of the sulphite oxidase due to the strong fluctuations. This is the main reason for the development of xanthin stones in classical human xanthinurea (Type 1) and finally is responsible for the failure of the kidneys and appears therewith to be the cause of death of the older treated animals after 70 days. Human xanthinurea remains however without symptom until the total failure of the xanthin-dehydrogenase activity in most cases$^{B29}$, and even in cases with symptoms there are seldom life threatening conditions. Thus, in this connection a supplemental influence of the sulphite oxidase deficiency on renal function must be taken into consideration. Thus the treatment of human Moco-deficiency should target primarily the reestablishment of the sulphite oxidase activity. Until the present no effective therapy for patients with Moco-deficiency has been described$^{B11}$. For the rare Type C deficiency, which is caused by gephyrin mutations, we have demonstrated the reestablishment in a fibroblast culture by means of Molybdate, which already suggests, that even small amounts of active Moco are sufficient for a reestablishment of the normal phenotype $^{B22}$ Since two thirds of the known Moco-deficient patients belong to deficiency Group A $^{B10, 12}$ and all components for a conversion of precursor Z to MPT must be present in these patients $^{B20,24}$, purified precursor Z provides the first potentially effective therapeutic for the most Moco-patients.

Intravenous administration of precursor Z is an attractive implementation option for human patients. This prenecessitates however not only a new magnitude of precursor Z production, in order to correspond to the approximately 1000-fold higher body weight of humans, and besides this the strong dilution before the active substance reaches the liver cells. Thus, in humans the use of a system permanently dispensing to the liver should be taken into consideration. Since the MOCS$^{-/-}$ mice correspond to the human phenotype in biochemical parameters, the treatment of the human deficiency with precursor Z on the level of enzymatic reestablishment and normalization of metabolism appears very promising.

It must be determined, whether a delayed initiation of the described therapy (which in most cases would be necessary due to the time required for clinical detection and diagnosis) is still suitable for preventing neurological damage. The described precursor Z therapy provides the basis to study the progression or reversal of this damage in detail, as we are now able to induce Moco deficiency in the animal model at any time by altering the dose of the drug. Tetrahydrobiopterin deficiency $^{B30}$ is a similar defect in biosynthesis of tetrhydrobiopterin, which leads loss of NO-synthases $^{B32}$ and the hydroxylases of aromatic amino acids $^{B31}$, which are essential for the synthesis of neurotransmitters (dopamine and serotonin). The possibility of the chemical synthesis enabled the first successful treatment of a patient of tetrahydrobioptern deficiency already in 1979 $^{B33, B34}$; which since then has become an established therapy $^{B30}$. Thus, the results of our work urgently indicate clinical tests for treatment of Moco-deficiency patients as soon as sufficient amounts of precursor Z can be produced.

LITERATURE

1. Hille, R. (1996) *Chem. Rev.* 96, 2757-2816
2. Stiefel, E. I. (1996) *Science* 272, 1599-1600
3. Enemark, J. H., and Cosper, M. M. (2002) *Met. Ions Biol. Syst.* 39, 621-654.
4. Mendel, R. R., Schwarz, G. (1999) *Crit. Rev. Plant Sci.* 18, 33-69
5. Johnson, J. L., Hainline, B. E., and Rajagopalan, K. V. (1980) *J. Biol. Chem.* 255, 1783-1786
6. Schindelin, H., Kisker, C., and Rajagopalan, K. V. (2001) *Adv. Protein Chem.* 58, 47-94
7. Mendel, R. R., and Schwarz, G. (2002) *Met. Ions Biol. Syst.* 39, 317-368
8. Duran, M., Beemer, F. A., van de Heiden, C., Korteland, J., de Bree, P. K., Brink, M., Wadman, S. K., and Lombeck, I. (1978) *J. Inherit. Metab. Dis.* 1, 175-178
9. Reiss, J., and Johnson, J. L. (2003) *Hum. Mutat.* 21, 569-576.
10. Johnson, J. L., and Duran, M. (2001) in *The metabolic and molecular bases of inherited disease* (Scriver, C., Beaudet, A., Sly, W., and Valle, D., eds), 8 Ed., pp. 3163-3177, McGraw-Hill, New York
11. Fischer, B., and Burgmayer, S. J. (2002) *Met. Ions Biol. Syst.* 39, 265-316.
12. Fischer, B., Enemark, J. H., and Basu, P. (1998) *J. Inorg. Biochem.* 72, 13-21.
13. Rajagopalan, K. V., and Johnson, J. L. (1992) *J. Biol. Chem.* 267, 10199-10202
14. Wuebbens, M. M., and Rajagopalan, K. V. (1993) *J. Biol. Chem.* 268, 13493-13498
15. Rieder, C., Eisenreich, W., O'Brien, J., Richter, G., Götze, E., Boyle, P., Blanchard, S., Bacher, A., and Simon, H. (1998) *Eur. J. Biochem.* 255, 24-36
16. Pitterle, D. M., and Rajagopalan, K. V. (1989) *J. Bacteriol.* 171, 3373-3378
17. Pitterle, D. M., Johnson, J. L., and Rajagopalan, K. V. (1993) *J. Biol. Chem.* 268, 13506-13509
18. Gutzke, G., Fischer, B., Mendel, R. R., and Schwarz, G. (2001) *J. Biol. Chem.* 276, 36268-36274.
19. Rudolph, M. J., Wuebbens, M. M., Rajagopalan, K. V., and Schindelin, H. (2001) *Nat. Struct. Biol.* 8, 4246.
20. Kuper, J., Palmer, T., Mendel, R. R., and Schwarz, G. (2000) *Proc. Natl. Acad. Sci. USA* 97, 6475-6480.
21. Nichols, J., and Rajagopalan, K. V. (2002) *J. Biol. Chem.* 277, 24995-25000.
22. Johnson, J. L., Bastian, N. R., and Rajagopalan, K. V. (1990) *Proc. Natl. Acad. Sci. U.S.A.* 87, 3190-3194
23. Rajagopalan, K. V. (1996) in *Escherichia coli* and *Salmonella typhimurium* (Neidhardt, F. C., ed), pp. 674-679, ASM Press, Washington D.C.
24. Romao, M. J., Archer, M., Moura, I., Moura, J. J., LeGall, J., Engh, R., Schneider, M., Hof, P., and Huber, R. (1995) *Science* 270, 1170-1176
25. Chan, M. K., Mukund, S., Kletzin, A., Adams, M. W. W., and Rees, D. C. (1995) *Science* 267, 1463-1469
26. Wuebbens, M. M., and Rajagopalan, K. V. (2003) *J. Biol. Chem.* 278, 14523-14532.
27. Doyle, W. A., Burke, J. F., Chovnick, A., Dutton, F. L., Whittle, J. R., and Bray, R. C. (1996) *Eur. J. Biochem.* 239, 782-795.
28. Johnson, J. L., Wuebbens, M. M., and Rajagopalan, K. V. (1989) *J. Biol. Chem.* 264, 13440-13447

29. Reiss, J., Kleinhofs, A., and Klingmuller, W. (1987) *Mol. Gen. Genet.* 206, 352-355

30. Rivers, S. L., McNairn, E., Blasco, F., Giordano, G., and Boxer, D. H. (1993) *Mol. Microbiol.* 8, 1071-1081

31. Leimkuhler, S., and Rajagopalan, K. V. (2001) *J. Biol. Chem.* 276, 22024-22031.

32. Schafer, A., Paul, H., Fischer, B., Hesse, M., and Visconfini, M. (1995) *Helv. Chim. Acta* 78, 1763-1776

33. Soyka, R., Pfleiderer, W., and Prewo, R. (1990) *Helv. Chim. Acta* 73, 808-826

34. Schindelin, H., Kisker, C., Hilton, J., Rajagopalan, K. V., and Rees, D. C. (1996) *Science* 272, 1615-1621

35. Kisker, C., Schindelin, H., Pacheco, A., Wehbi, W. A., Garrett, R. M., Rajagopalan, K. V., Enemark, J. H., and Rees, D. C. (1997) *Cell* 91, 973-983

36. Pfleiderer, W. (1996) in *Comprehensive Heterocyclic Chemistry* (Katritzky, A. R., Reese, C. W., and Scriven, E. F., eds) Vol. 7, pp. 679, Pergamon, Oxford 37. Bracher, A., Eisenreich, W., Schramek, N., Ritz, H., Gotze, E., Herrmann, A., Gutlich, M., and Bacher, A. (1998) *J. Biol. Chem.* 273, 28132-28141.

38. Irby, R. B., and Adair, W. L., Jr. (1994) *J. Biol. Chem.* 269, 23981-23987

39. Wuebbens, M. M., and Rajagopalan, K. V. (1995) *J. Biol. Chem.* 270, 1082-1087

40. Hanzelmann, P., Schwarz, G., and Mendel, R. R. (2002) *J. Biol. Chem.* 277, 18303-18312

B1. Rajagopalan, K. V. & Johnson, J. L. The pterin molybdenum cofactors. *J. Biol. Chem.* 267, 10199-10202 (1992).

B2. Wahl, R. C., Hageman, R. V. & Rajagopalan, K. V. The relationship of Mo, molybdopterin, and the cyanolyzable sulfur in the Mo cofactor. *Arch. Biochem. Biophys.* 230, 264-273 (1984).

B3. Reiss, J. et al. Mutations in a polycistronic nuclear gene associated with molybdenum cofactor deficiency. *Nat. Genet.* 20, 51-53 (1998).

B4. Stallmeyer, B., Drugeon, G., Reiss, J., Haenni, A. L. & Mendel, R. R. Human molybdopterin synthase gene: identification of a bicistronic transcript with overlapping reading frames. *Am. J. Hum. Genet.* 64, 698-705 (1999).

B5. Stallmeyer, B. et al. The neurotransmitter receptor-anchoring protein gephyrin reconstitutes molybdenum cofactor biosynthesis in bacteria, plants, and mammalian cells. *Proc. Natl. Acad. Sci. U.S.A.* 96, 1333-1338 (1999).

B6. Mendel, R. R. & Schwarz, G. Biosynthesis and molecular biology of the molybdenum cofactor (Moco). *Met. Ions Biol. Syst.* 39, 317-368. (2002).

B7. Rajagopalan, K. V. Biosynthesis of the molybdenum cofactor. in *Escherichia coli* and *Salmonella typhimurium* (ed. Neidhardt, F. C.) 674-679 (ASM Press, Washington D. C., 1996).

B8. Duran, M. et al. Combined deficiency of xanthine oxidase and sulphite oxidase: a defect of molybdenum metabolism or transport? *J. Inherit. Metab. Dis.* 1, 175-178 (1978).

B9. Johnson, J. L. et al. Inborn errors of molybdenum metabolism: combined deficiencies of sulfite oxidase and xanthine dehydrogenase in a patient lacking the molybdenum cofactor. *Proc. Natl. Acad. Sci. U.S.A.* 77, 3715-3719. (1980).

B10. Reiss, J. Genetics of molybdenum cofactor deficiency. *Hum. Genet.* 106, 157-163. (2000).

B11. Johnson, J. L. & Duran, M. Molybdenum cofactor deficiency and isolated sulfite oxidase deficiency. in *The metabolic and molecular bases of inherited disease* (eds. Scriver, C., Beaudet, A., Sly, W. & Valle, D.) 3163-3177 (McGraw-Hill, New York, 2001).

B12. Reiss, J. & Johnson, J. L. Mutations in the molybdenum cofactor biosynthetic genes MOCS1, MOCS2, and GEPH. *Hum. Mutat.* 21, 569-576. (2003).

B13. Johnson, J. L. et al. Molybdopterin synthase mutations in a mild case of molybdenum cofactor deficiency. *Am. J. Med. Genet.* 104, 169-173. (2001).

B14. Johnson, J. L., Rajagopalan, K. V. & Wadman, S. K. Human molybdenum cofactor deficiency. *Adv. Exp. Med. Biol.* 338, 373-378 (1993).

B15. Hoff, T., Schnorr, K. M., Meyer, C. & Caboche, M. Isolation of two *Arabidopsis* cDNAs involved in early steps of molybdenum cofactor biosynthesis by functional complementation of *Escherichia coli* mutants. *J. Biol. Chem.* 270, 6100-6107 (1995).

B16. Gray, T. A. & Nicholls, R. D. Diverse splicing mechanisms fuse the evolutionarily conserved bicistronic MOCS1A and MOCS1B open reading frames. *RNA* 6, 928-936 (2000).

B17. Hanzelmann, P., Schwarz, G. & Mendel, R. R. Functionality of alternative splice forms of the first enzymes involved in human molybdenum cofactor biosynthesis. *J. Biol. Chem.* 277, 18303-18312 (2002).

B18. Gross-Hardt, S. & Reiss, J. The bicistronic MOCS1 gene has alternative start codons on two mutually exclusive exons. *Mol. Genet. Metab.* 76, 340-343 (2002).

B19. Wuebbens, M. M. & Rajagopalan, K. V. Structural characterization of a molybdopterin precursor. *J. Biol. Chem.* 268, 13493-13498 (1993).

B20. Johnson, J. L., Wuebbens, M. M., Mandell, R. & Shih, V. E. Molybdenum cofactor biosynthesis in humans. Identification of two complementation groups of cofactor-deficient patients and preliminary characterization of a diffusible molybdopterin precursor. *J. Clin. Invest.* 83, 897-903 (1989).

B21. Reiss, J. et al. Human molybdopterin synthase gene: genomic structure and mutations in molybdenum cofactor deficiency type B. *Am. J. Hum. Genet.* 64, 706-711 (1999).

B22. Reiss, J. et al. A mutation in the gene for the neurotransmitter receptor-clustering protein gephyrin causes a novel form of molybdenum cofactor deficiency. *Am. J. Hum. Genet.* 68, 208-213. (2001).

B23. Johnson, J. L., Wuebbens, M. M. & Rajagopalan, K. V. The structure of a molybdopterin precursor. Characterization of a stable, oxidized derivative. *J. Biol. Chem.* 264, 13440-13447 (1989).

B24. Johnson, J. L. & Rajagopalan, K. V. Molybdopterin biosynthesis in man. Properties of the converting factor in liver tissue from a molybdenum cofactor deficient patient. *Adv. Exp. Med. Biol.* 338, 379-382 (1993).

B25. Lee, H.-J. et al. Molybdenum cofactor-deficient mice resemble the phenotype of human patients. *Hum. Mol. Gen.* 11, 3309-3317 (2002).

B26. Gutzke, G., Fischer, B., Mendel, R. R. & Schwarz, G. Thiocarboxylation of molybdopterin synthase provides evidence for the mechanism of dithiolene formation in metal-binding pterins. *J. Biol. Chem.* 276, 36268-36274. (2001).

B27. Ono, H. & Ito, A. Transport of the precursor for sulfite oxidase into intermembrane space of liver mitochondria: characterization of import and processing activities. *J. Biochem.* (Tokyo) 95, 345-352. (1984).

B28. Falciani, F., Ghezzi, P., Terao, M., Cazzaniga, G. & Garattini, E. Interferons induce xanthine dehydrogenase gene expression in L929 cells. *Biochem. J.* 285, 1001-1008. (1992).

B29. Simmonds, H. A., Reiter, S. & Nishino, T. Hereditary xanthinuria. in *The metabolic and molecular bases of*

*inherited disease* (eds. Scriver, C. R., Beaudet, A. L., Sly, W. S. & Valle, D.) 1781-1797 (McGraw-Hill, New York, 1995).

B30. Blau, N., Thöny, B., Cotton, R. G. H. & Hyland, K. Disorders of Tetrahydrobiopterin and Related Biogenic Amines. in *The metabolic and molecular bases of inherited disease* (eds. Scriver, C., Beaudet, A., Sly, W. & Valle, D.) 1725-1776 (McGraw-Hill, New York, 2001).

B31. Fitzpatrick, P. F. Tetrahydropterin-dependent amino acid hydroxylases. *Annu. Rev. Biochem.* 68, 355-381. (1999).

B32. Alderton, W. K., Cooper, C. E. & Knowles, R. G. Nitric oxide synthases: structure, function and inhibition. *Biochem. J.* 357, 593-615. (2001).

B33. Schircks, B., Bieri, J. H. & Viscontini, M. [Preparation and characterisation of pure 5,6,7,8-tetrahydro-L-neopterine and 5,6,7,8-tetrahydro-D-monapterine (author's transl)]. *Helv. Chim. Acta* 59, 248-252. (1976).

B34. Niederwieser, A., Curtius, H. C., Viscontini, M., Schaub, J. & Schmidt, H. Phenylketonuria variants. *Lancet* 1, 550. (1979).

B35. Rivers, S. L., McNairn, E., Blasco, F., Giordano, G. & Boxer, D. H. Molecular genetic analysis of the moa operon of *Escherichia coli* K-12 required for molybdenum cofactor biosynthesis. *Mol. Microbiol.* 8, 1071-1081 (1993).

B36. Reiss, J., Kleinhofs, A. & Klingmuller, W. Cloning of seven differently complementing DNA fragments with ch1 functions from *Escherichia coli* K12. *Mol. Gen. Genet.* 206, 352-355 (1987).

B37. Leimkuhler, S. & Rajagopalan, K. V. A sulfurtransferase is required in the transfer of cysteine sulfur in the in vitro synthesis of molybdopterin from precursor Z in *Escherichia coli*. *J. Biol. Chem.* 276, 22024-22031. (2001).

B38. Nason, A. et al. Invitro formation of assimilatory reduced nicotinamide adenine dinucleotide phosphate: nitrate reductase from a *Neurospora* mutant and a component of molybdenum-enzymes. *Proc. Natl. Acad. Sci. U S A* 68, 3242-3246 (1971).

B39. Morris, R. Developments of a water-maze procedure for studying spatial learning in the rat. *J. Neurosci. Methods* 11, 47-60. (1984).

B40. Schwarz, G., Boxer, D. H. & Mendel, R. R. Molybdenum cofactor biosynthesis. The plant protein Cnx1 binds molybdopterin with high affinity. *J. Biol. Chem.* 272, 26811-26814 (1997).

B41. Johnson, J. L. et al. Prenatal diagnosis of molybdenum cofactor deficiency by assay of sulphite oxidase activity in chorionic villus samples. *J. Inherit. Metab. Dis.* 14, 932-937 (1991).

B42. Mendel, R. R. & Müller, A. J. A common genetic determinant of xanthine dehydrogenase and nitrate reductase in *Nicotiana tabacum. Biochem. Physiol. Pflanzen* 170, 538-541 (1976).

B43. Koshiba, T., Saito, E., Ono, N., Yamamoto, N. & Sato, M. Purification and properties of flavin- and molybdenum containing aldehyde oxidase from coleoptyles of maize. *Plant Physiol.* 110, 781-789 (1996).

The following abbreviations were employed:

1D, one-dimensional; 2D, two-dimensional; COSY, Correlation-Spectroscopy; ESI, Electrospray-ionisation; Moco, Molybdenum-cofaktor; MS, mass spectrometry; MPT, Molybdopterin or Metal-binding Pyranopterin-Dithiol; Mo, Molybdenum; NMR Nuclear Magnetic Resonance; W, Titanium.

What is claimed is:

1. A therapeutic composition for treatment of human molybdenum cofactor deficiency and associated diseases that can be directly or indirectly traced back to a corrupted molybdenum cofactor synthesis, said composition comprising precursor Z and a pharmaceutically acceptable carrier, wherein precursor Z has the following chemical structure:

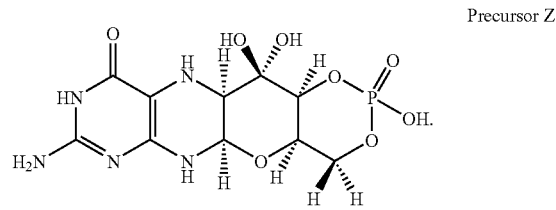

Precursor Z

2. A method for treatment of a human with molybdenum cofactor deficiency and associated diseases that can be directly or indirectly traced back to a corrupted molybdenum cofactor synthesis, said method comprising administering to said human a therapeutically effective amount of the therapeutic composition of claim 1.

* * * * *